US009164086B2

(12) United States Patent
Hell et al.

(10) Patent No.: US 9,164,086 B2
(45) Date of Patent: Oct. 20, 2015

(54) FLUORESCENT DYES WITH PHOSPHORYLATED HYDROXYMETHYL GROUPS AND THEIR USE IN LIGHT MICROSCOPY AND IMAGING TECHNIQUES

(75) Inventors: Stefan W. Hell, Goettingen (DE); Shamil Nizamov, Goettingen (DE); Gerald Donnert, Hoechberg (DE); Kirill Kolmakov, St. Petersburg (RU); Heiko Schill, Goettingen (DE); Lars Kastrup, Goettingen (DE); Christian A. Wurm, Goettingen (DE); Vladimir N. Belov, Goettingen (DE); Johanna Wildanger, Uedem (DE); Katrin Willig, Goettingen (DE)

(73) Assignee: Max-Planck-Gesellschaft zur Foerderung der Wissenschaften e.V., Munich (DE)

( * ) Notice: Subject to any disclaimer, the term of this patent is extended or adjusted under 35 U.S.C. 154(b) by 0 days.

(21) Appl. No.: 13/702,252

(22) PCT Filed: Oct. 18, 2011

(86) PCT No.: PCT/EP2011/005231
§ 371 (c)(1),
(2), (4) Date: Feb. 20, 2013

(87) PCT Pub. No.: WO2013/056720
PCT Pub. Date: Apr. 25, 2013

(65) Prior Publication Data
US 2014/0220588 A1 Aug. 7, 2014

(51) Int. Cl.
*C09B 57/02* (2006.01)
*G01N 33/52* (2006.01)
*C09B 11/24* (2006.01)
*C09B 57/10* (2006.01)
*G01N 33/58* (2006.01)
*G01N 33/533* (2006.01)

(52) U.S. Cl.
CPC ................ *G01N 33/52* (2013.01); *C09B 11/24* (2013.01); *C09B 57/02* (2013.01); *C09B 57/10* (2013.01); *G01N 33/533* (2013.01); *G01N 33/582* (2013.01); *G01N 2458/00* (2013.01)

(58) Field of Classification Search
CPC .................................................... C09B 57/02
See application file for complete search history.

(56) References Cited

U.S. PATENT DOCUMENTS

| 4,774,339 | A | 9/1988 | Haugland et al. |
| 5,756,771 | A | 5/1998 | Mattingly |
| 6,130,101 | A | 10/2000 | Mao et al. |
| 6,372,907 | B1 | 4/2002 | Lee et al. |
| 7,563,907 | B2 | 7/2009 | Czerney et al. |
| 2003/0165942 | A1 | 9/2003 | Czerney et al. |
| 2004/0260093 | A1 | 12/2004 | Czerney et al. |
| 2006/0179585 | A1 | 8/2006 | Zilles et al. |
| 2006/0199955 | A1 | 9/2006 | Lukhtanov et al. |
| 2007/0249014 | A1 | 10/2007 | Agnew et al. |
| 2008/0311041 | A1 | 12/2008 | Verkman et al. |
| 2011/0172420 | A1 | 7/2011 | Zilles et al. |
| 2011/0190486 | A1 | 8/2011 | Zilles et al. |

FOREIGN PATENT DOCUMENTS

| EP | 1016661 A1 | 7/2000 |
| EP | 1318177 B1 | 9/2004 |
| EP | 2253635 A1 | 11/2010 |
| WO | 9739326 A2 | 10/1997 |
| WO | 9915517 A1 | 4/1999 |
| WO | 2004027084 A1 | 4/2004 |
| WO | 2005003086 A2 | 1/2005 |
| WO | 2008151089 A2 | 12/2008 |
| WO | 2009078970 A1 | 6/2009 |
| WO | 2010083471 A1 | 7/2010 |
| WO | 2010124833 A1 | 11/2010 |
| WO | 2010149190 A1 | 12/2010 |

OTHER PUBLICATIONS

Bannwarth et al., "Bis(Allyloxy)(Diisopropylamino) Phosphine as a New Phosphinylation Reagent for the Phosphorylation of Hydroxy Functions", Tetrahedron Lett., vol. 30, No. 32, pp. 4219-4222 (1989).
Berlier et al., "Quantitative Comparison of Long-wavelength Alexa Fluor Dyes to Cy Dyes: Fluorescence of the Dyes and Their Bioconjugates", J. Histochem. Cytochem., vol. 51 (12), pp. 1699-1712 (2003).
Boyarskiy et al., "Photostable, Amino Reactive and Water-Soluble Fluorescent Labels Based on Sulfonated Rhodamine with a Rigidized Xanthene Fragment", Chem. Eur. J., vol. 14, pp. 1784-1792 (2008).
Chaleix et al., "RGD-Porphyrin Conjugates: Synthesis and Potential Application in Photodynamic Therapy", Eur. J. Org. Chem., pp. 1486-1493 (2003).
Corey et al., "An Enantioselective Synthesis of (6R)-Lactacystin", Tetrahedron Letters, vol. 34, No. 44, pp. 6969-6972 (1993).
Durgam et al., "Synthesis, Structure-Activity Relationships, and Biological Evaluation of Fatty Alcohol Phospates as Lyso-phosphatidic Acid Receptor Ligands, Activators of PPARγ, and Inhibitors of Autotaxin", J. Med. Chem., vol. 48, pp. 4919-4930 (2005).
Glenn et al. "Antiproliferative and Phenotype-Transforming Antitumor Agents Derived from Cysteine", J. Med. Chem., vol. 47, pp. 2984-2994 (2004).
Haugland, "A Guide to Fluorescent Probes and Labeling Technologies", Invitrogen, Carlsbad, pp. 11-37, pp. 77-78 (2005).
Hayakawa et al., "Allyloxycarbonyl Group: A Versatile Blocking Group for Nucleotide Synthesis", J. Org. Chem., vol. 51, pp. 2400-2402 (1986).
Hell, "Far-Field Optical Nanoscopy", in Single Molecule Spectroscopy in Chemistry, Physics and Biology, pp. 365-390 (2010).
Kolmakov et al., "Red-Emitting Rhodamine Dyes for Fluorescence Microscopy and Nanoscopy", Chem. Eur. J., vol. 16, pp. 158-166 (2010).
Krumova et al., "Bodipy Dyes with Tunable Redox Potentials and Functional Groups for Further Tethering: Preparation, Electrochemical, and Spectroscopic Characterization", J. Am. Chem. Soc., vol. 132, pp. 17560-17569 (2010).
Mashraqui et al. "Efficient Synthesis of 3-Substituted Coumarins", Synth. Comm., vol. 34, No. 17, pp. 3129-3134 (2004).
Ohnuki et al., "Practical Phosphorylation Methods for a,a-Di-substituted α-Amino Alcohol Derivatives", Synlett, No. 6, pp. 910-912 (2009).
Perich et al., "Di-tert-butyl N,N-Diethyl¬ phosphoramidite. A New Phosphitylating Agent for the Efficient Phosphorylation of Alcohols", Synthesis, vol. 2, pp. 142-144 (1988).
Sathyamoorthi et al., "Selective Side-Chain Oxidation of Peralkylated Pyrromethene-BF2 Complexes", Heteroatom Chemistry, vol. 5, No. 3, pp. 245-249 (1994).

Senda et al., "Synthesis and Photochemical Properties of a New Water-Soluble Coumarin, Designed as a Chromophore for Highly Water-Soluble and Photolabile Protecting Group", Bull. Chem Soc. Jpn. vol. 79, No. 11, pp. 1753-1757 (2006).

Theoclitou et al., "Novel facile synthesis of 2,2,4 substituted 1,2-dihydroquinolines via a modified Skraup reaction", Tetrahedron Letters, vol. 43, pp. 3907-3910 (2002).

International Search Report for PCT/EP2011/005231 dated Mar. 7, 2013.

*Primary Examiner* — Joseph Kosack

(74) *Attorney, Agent, or Firm* — Caesar Rivise, PC

(57) ABSTRACT

The invention relates to novel fluorescent dyes with phosphorylated hydroxymethyl groups, a method for preparing the same as well as to their use in imaging techniques. The fluorescent dyes are coumarin, rhodamine or BODIPY dyes having of one of the following general formulae I-III:

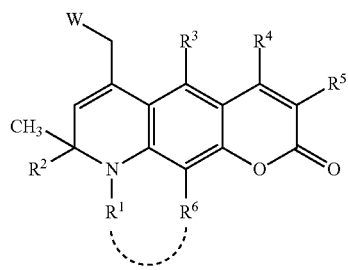

Ia

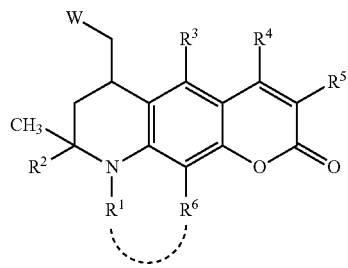

Ib

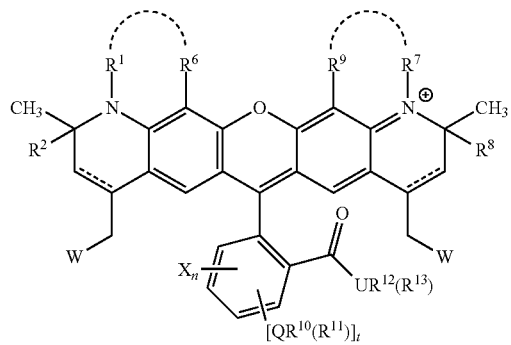

IIa

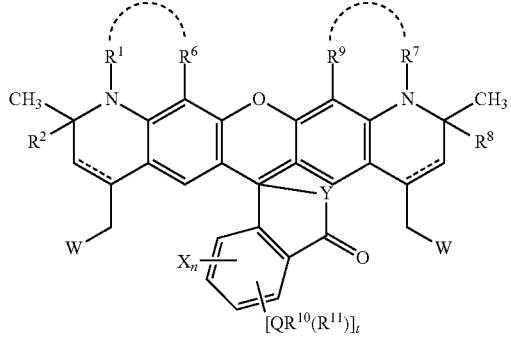

IIb

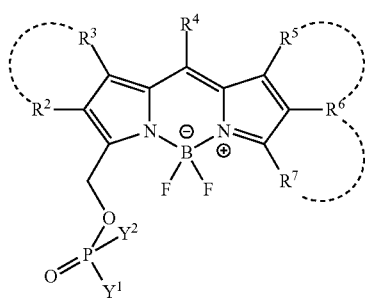

IIIa

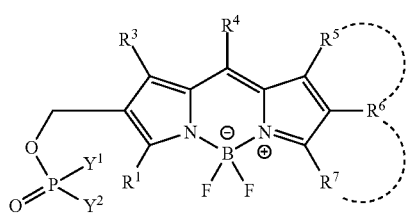

IIIb

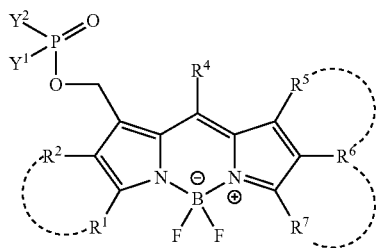

IIIc

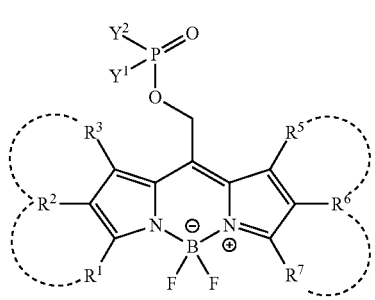

IIId wherein $W=OP(O)Y^1Y^2$ or $P(O)Y^1Y^2$, where $Y^1$ and $Y^2$ independently denote any of the following residues: OH, O(–), $OR^a$ and $OR^b$, $NHR^a$ and $NHR^b$, $NR^aR^b$ and $NR^cR^d$, $OR^a$ and $NHR^b$, $OR^a$ and $NR^bR^c$, $NHR^a$ and $NR^bR^c$; and any salt thereof.

10 Claims, 4 Drawing Sheets
(4 of 4 Drawing Sheet(s) Filed in Color)

FLUORESCENT DYES WITH PHOSPHORYLATED HYDROXYMETHYL GROUPS AND THEIR USE IN LIGHT MICROSCOPY AND IMAGING TECHNIQUES

BACKGROUND OF THE INVENTION

Coumarin and rhodamine dyes are known as bright fluorescent labels with large absorption coefficients, high fluorescent quantum yields, and low degree of triplet formation. They are widely used both as laser dyes and fluorescent compounds for labeling proteins, nucleic acids, lipids, carbohydrates, toxins, hormones and other biomolecules (for examples, see: R. P. Haugland, *A Guide to Fluorescent Probes and Labeling Technologies*, Invitrogen, Carlsbad, 2005, pp. 11-37, 77-78).

Rhodamines are generally more photostable than coumarins. Therefore they are often applied for practical implementations of new physical concepts that require high light intensities and/or the detection of the single photostable and fluorescent molecules. For example, it was demonstrated that the diffraction limit of an optical microscope can be overcome by switching between the dark and bright states of a fluorescent marker (S. W. Hell, in *Single Molecule Spectroscopy in Chemistry, Physics and Biology*, Eds: A. Gräslund, R. Rigler, J. Widengren, Springer, Berlin, 2010, pp. 365-398). In particular, a very important novel method, the stimulated emission depletion (STED) microscopy, uses the ground (singlet) state of the fluorophore ($S_0$) as a dark state, and the first excited state ($S_1$) as a bright one. In practical applications of the STED method, a focused pulse excites fluorescence in a small spot (with dimensions limited by diffraction), and then a red-shifted doughnut-shaped STED beam switches off the fluorescence of the excited molecules by stimulated emission ($S_1 \rightarrow S_0$) everywhere, except in the very center of the doughnut, where the quenching intensity is zero. For squeezing the fluorescence to a very small central spot, the depletion rate should exceed the rate of the spontaneous transition to the ground state $S_0$. Fluorescent lifetimes of organic fluorophores ($\tau_{fl} \sim 10^{-9}$ s) and their optical cross-sections of the $S_1 \rightarrow S_0$ transitions ($\sigma \sim 10^{-16}$ cm$^2$) imply that the STED-pulse should have a very high power $I_{STED} \gg I_S \equiv (\sigma \tau_{fl})^{-1} \sim 10^{25}$ photons/(cm$^2 \times$s)$\cong$10 MW/cm$^2$. ($I_S$ is a threshold intensity depending on the dye employed and the depletion wavelength used.) The resolution enhancement scales roughly with $\sqrt{1+I_{STED}/I_S}$.

These huge light intensities inevitably cause photobleaching of fluorophores, and therefore STED microscopy ultimately requires the most photostable fluorescent dyes. The far-field optical "nanoscopy" based on the STED principle provides an optical resolution of 30-60 nm with organic fluorophores.

Along with the relatively long lifetimes of the excited states (e.g. 1-20 ns), other important qualities of the STED and common fluorescent dyes are high fluorescent quantum yields ($\Phi_{fl}$) and oscillator strengths (high absorption coefficients, $\epsilon$), low rate of triplet state formation, sufficient solubility in water or aqueous buffers and a reactive group (with a linker) for attaching the dye to a biological object or any other structure of interest. High $\Phi_{fl}$-values of the fluorescent labels conjugated with biomolecules are very important, as they improve the sensitivity of the imaging method. Moreover, if a resolution on the molecular scale is desired, or if only single molecules remain in the effective detection volume, the fluorescent dyes should be suitable for single molecule detection (e.g. in the method of fluorescence correlation spectroscopy—FCS).

Water is the preferred solvent for operating with the reactive fluorescent dyes, because the conjugation reactions involving biologically relevant macromolecules (proteins, nucleic acids, carbohydrates, etc.) need to be performed in water or aqueous buffers. A marker is usually dissolved in an organic solvent, such as DMF or DMSO, and then added to the aqueous solution of the substrate. High concentrations of an organic solvent may cause protein denaturizing, and hence should be avoided. On the other hand, a low coupling efficiency may be observed if the amount of the organic solvent is too low and the marker precipitates in the reaction mixture. Water-soluble fluorescent markers are advantageous in this regard, because they do not require any organic solvents at all. Moreover, hydrophilic labels are less prone to aggregation and to non-specific binding with biological objects, especially membranes.

Biological applications require fluorescent dyes absorbing and emitting in the red spectral region, because the excitation in this area reduces the background originating from autofluorescence of the cells (evident with UV and blue excitation). Very convenient is the excitation by the red He—Ne laser at 633 nm or with the 635 nm spectral line of a red diode laser, as well as with the 647 nm line of the krypton ion laser or with a diode laser emitting at 650 nm. For two-color applications with coumarin and rhodamine dyes, diode lasers emitting at 405 nm or 488 nm, respectively, constitute other convenient excitation sources.

Another important feature of a fluorescent dye is the Stokes shift (distance between the absorption and emission maxima measured in nm or cm$^{-1}$). Fluorescent dyes with large Stokes shifts can be used alone or together with emitters possessing small Stokes shifts in various imaging techniques. For example, a pair of dyes emitting approximately at the same wavelength with well separated absorption bands may be used for labeling, detection and colocalization of two different (biological) targets. A great advantage of this approach is that only one detection channel is used. The "cross-talk" observed in the course of the excitation with two different light sources (lasers) has to be low. Photostable and brightly fluorescent dyes with large Stokes shifts are rare and only few of them are commercially available. Many of these dyes contain a coumarin fragment as the fluorophore. For example, the "Mega Stokes" dyes from Dyomics are coumarins absorbing at about 500-520 nm, and emitting in the region of 590-670 nm [P. Czerney, M. Wenzel, B. Schwender, F. Lehmann, EP 1318177 B1, 5 Dec. 2002; U.S. Pat. No. 7,563,907 B2, 21 Jul. 2009]. Another practically useful coumarin dye is Alexa Fluor™ 430 with an absorption maximum at 434 nm and an emission band at 539 nm (Invitrogen). However, the chemical structures of many commercially available fluorescent dyes with large Stokes shifts are unknown. For example the structures of Pacific Orange™ (abs. 390 nm, emission 540 nm; Invitrogen) and V500 (abs. 410 nm, emission 500 nm; BD Horizon™) have not been disclosed. The common features of coumarin dyes are large Stokes shifts, as well as moderate photostability and relatively low fluorescence quantum yields in polar solvents.

Analysis of the disclosed structures of the commercial fluorescent dyes matching the excitation with a red He—Ne laser (633 nm) or the 635 nm spectral line of red diode lasers reveals that there is only one rhodamine among them: Alexa 633 was reported to be a "sulfonated rhodamine derivative" [J. E. Berlier et al., *J. Histochem. Cytochem.* 2003, 51, 1699-1712], and only in 2007 its structure has been reported [B. Agnew, K. R. Gee, T. G. Nyberg (Invitrogen), US Pat. 2007/0249014]. Up to now, the highest values for the adsorption and emission maxima have been achieved for rhodamines with a rigidized xanthene fragment obtained from tetrafluoro- or tetrachlorophthalic anhydrides. For example, absorption and emission maxima of 630 and 655 nm, respectively, have been observed in 8 M urea solution [L. G. Lee, R. J. Graham, W. E. Werner, E. Swartzman, L. Lu, (Apptera Corp., USA), U.S. Pat. No. 6,372,907 (16 Apr. 2002)]. The disadvantage of the fluorescent dye with four fluorine atoms disclosed in the document cited above is its high lipophilicity (low polarity) and therefore low solubility in water or aqueous buffers. Another drawback of this compound (as well as tetrachloro rhodamine JA 407 [compound 40 in WO 2005/003086] is that they have a free carboxylic group which may give a colorless and non-fluorescent cyclic ester form. Similar spectral values (624 and 644 nm for the absorption and emission, respectively) have been recorded in ethanol for ethyl esters of the tetrachloro rhodamines JA 407-E and AZ 84-AZ 95 [compounds 41 and 71-82 in WO 2005/003086].

Though rhodamine dyes disclosed in U.S. Pat. No. 6,372, 907 and in WO 2005/003086 represent valuable intermediates, they lack any suitable reactive site for an attachment to biomolecules. The carboxylic group (COOH) on the benzene ring in the ortho position to the xanthene fragment in the compounds described in U.S. Pat. No. 6,372,907, as well as the COOH-group in the acid JA 407 [compound 40 in WO 2005/003086] are sterically hindered and therefore, less reactive. Moreover, the reaction of this carboxylic acid with primary amino groups (e.g. in various biomolecules, like peptides, proteins, lipids, etc.) would give amides which are known to form colorless and non-fluorescent cyclic spiroamides (due to addition of the NH-group across the tetrasubstituted $C^9=C^{8a/8b}$ double bond in the central xanthene ring).

Some drawbacks of the red-emitting rhodamines mentioned above were overcome in EP 2253635 (WO2010124833) in which new photostable, bright, amino and thiol reactive rhodamines for labeling and imaging have been disclosed. However, the fluorescence quantum yield decreased considerably after conjugation with antibodies (from 78-80% to 40-48%, depending on the nature of the protein), and the stability of the active esters was found to be rather low.

The alteration in the fluorescence quantum yield after bioconjugation (compared to that of a free dye in an aqueous buffer solution) is a very important issue. In the course of the labeling procedure, a fluorescent dye is bound to a protein (e.g. streptavidin, primary or secondary antibodies, etc.), and the fluorescence signal of the bioconjugate (which is very often further diluted in the course of the immunolabeling procedure) is observed in a light microscope.

As a rule, the high fluorescence quantum yield of a (hydrophilic) fluorescent dye decreases upon biocojugation [a] V. P. Boyarskiy, V. N. Belay, R. Medda, B. Hein, M. Bossi, S. W. Hell, Chem. Eur. J. 2008, 14, 1784-1792; b) K. Kolmakov, V. N. Belay, J. Bierwagen, C. Ringemann, V. Müller, C. Eggeling, S. W. Hell, Chem. Eur. J. 2010, 16, 158-166]. For obvious reasons, there is a great demand of fluorescent dyes with a minimal decrease in the fluorescence quantum yield caused by bioconjugation.

In view of the drawbacks of the fluorescent dyes of the prior art, the main object of the present invention was to provide a novel general approach to hydrophilic fluorescent dyes with improved properties, namely photostability in aqueous solutions, solubility in pure water and aqueous buffers, high values for fluorescence quantum yield in the free state and after conjugation with proteins, which would be suitable for microscopy applications with very high light intensities such as STED and FCS.

This objective has been achieved by providing novel fluorescent dyes with phosphorylated hydroxymethyl groups according to claims 1-3, a method for preparing such dyes which are phosphorylated coumarins and rhodamines according to claims 4 and 5, precursor compounds for the synthesis of said coumarins and rhodamines according to claims 6 and 7, as well as the uses of the disclosed novel fluorescent dyes according to claims 8-11.

DESCRIPTION OF THE INVENTION

The novel fluorescent dyes with phosphorylated hydroxymethyl groups of the invention are selected from the group consisting of compounds of the following general formulae I-III:

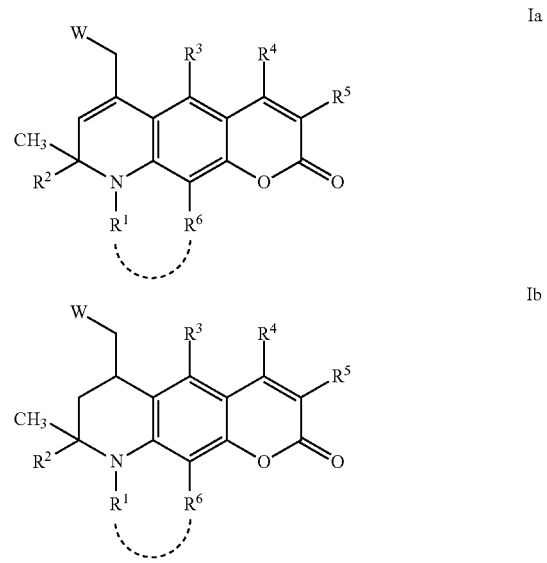

wherein
$R^1$ denotes H, $CH_3$, $C_2H_5$, any other alkyl, cycloalkyl, alkenyl, alkynyl, aryl, arylalkyl or heteroaryl group; (functionally) substituted alkyl, cycloalkyl, alkenyl, alkynyl, aryl, arylalkyl or heteroaryl group; heterosubstituted alkyl or cycloalkyl group, e.g. azacycloalkyl, azaoxacycloalkyl, oxaalkyl, $(CH_2CH_2O)_mCH_3$ (m=0-24); $(CH_2)_mCH_2OP(O)$ $Y^1Y^2$, where $Y^1$ and $Y^2$ independently denote any of the following residues: OH, O(−), $OR^a$ and $OR^b$, $NHR^a$ and $NHR^b$, $NR^aR^b$ and $NR^cR^d$, $OR^a$ and $NHR^b$, $OR^a$ and $NR^bR^c$, $NHR^a$ and $NR^bR^c$; or $R^1$ may represent the combination of the said groups; in particular, $R^1$ may denote an acid group $(CH_2)_mCOOH$ (m=0-23) or an ester $(CH_2)_m COOR^a$, as well as primary amide $(CH_2)_mCONHR^a$ or secondary amide $(CH_2)_mCONR^aR^b$ (m=0-23); oligo(ethylene glycol) derivatives with a carboxylic acid group $(CH_2CH_2O)_mCH_2(CH_2)_nCOOH$ (m=0-23; n=0,1), and the corresponding esters $(CH_2CH_2O)_mCH_2(CH_2)_nCOOR^a$, as well as primary amides $(CH_2CH_2O)_m(CH_2)_nCONHR^b$ and secondary amides $(CH_2CH_2O)_m(CH_2)_nCONR^cR^d$ (m=0-23; n=0,1); $R^a$, $R^b$, $R^c$ and $R^d$ independently denote separate substituents like H, alkyl, cycloalkyl, alkenyl, e.g. allyl, alkynyl, e.g. propargyl, aryl, e.g. phenyl, a heterosubstituted alkyl or cycloalkyl group, e.g. azacycloalkyl, oxaalkyl, haloacetylaminoalkyl, a functionally substituted alkyl group, e.g. ω-azidoalkyl, ω-(N-maleimido)alkyl, a heterocyclic residue, e.g. N-succinimidyl, heteroaryl, e.g.

4-pyridyl, (functionally) substituted aryl, e.g. perfluorophenyl, (functionally) substituted heteroaryl, e.g. 4-pyridyloxy, or $R^a$ and $R^b$ ($R^c$ and $R^d$) form a cyclic system [only in the case of secondary amides, where $R^1$=$(CH_2)_m$CONR$^a$R$^b$, or $(CH_2CH_2O)_m$CONR$^a$R$^b$, or $R^1$=$(CH_2)_m$CH$_2$OP(O)(NR$^a$R$^b$)(NR$^c$R$^d$)];

$R^2$=CH$_3$, alkyl, HOCH$_2$, hydroxyalkyl, alkoxyalkyl;

$R^3$ and $R^6$ independently denote H, F, Cl, CH$_3$, or any other alkyl group; alternatively, $R^1$ - - - $R^6$=—(CH$_2$)$_2$—, —(CH$_2$)$_3$—, —CH$_2$COCH$_2$—, —CH$_2$[C=N(OR$^a$)]CH$_2$— or —CH$_2$(C=N—NR$^a$R$^b$)CH$_2$—, with $R^a$ and $R^b$ as defined above;

$R^4$=H, CH$_3$, alkyl, OR$^a$, (CH$_2$)$_m$COOR$^a$, (CH$_2$)$_m$CH$_2$OR$^a$, (CH$_2$)$_m$COOR$^a$, (CH$_2$)$_m$CONR$^a$R$^b$ (m=0-23), with $R^a$ and $R^b$ as defined above;

$R^5$=aryl, heteroaryl, e. g. 2-pyridyl, 4-pyridyl, pyrimidin-2-yl, pyrimidin-3-yl, pyrimidin-4-yl, pyrazin-2-yl, pyridazin-3-yl, pyridazin-4-yl, 1,3,5-triazinyl, 1,2,4-triazin-3-yl; (functionally) substituted aryl or heteroaryl, CF$_3$, perfluoroalkyl (C$_n$F$_{2n+1}$), CN, C≡CR$^a$, i.e. alkyne with the definition of $R^a$ as given above;

W=OP(O)Y$^1$Y$^2$ or P(O)Y$^1$Y$^2$ where Y$^1$ and Y$^2$ independently denote any of the following residues: OH, O(–), OR$^a$ and OR$^b$, NHR$^a$ and NHR$^b$, NR$^a$R$^b$ and NR$^c$R$^d$, OR$^a$ and NHR$^b$, OR$^a$ and NR$^b$R$^c$, NHR$^a$ and NR$^b$R$^c$; and any salt thereof;

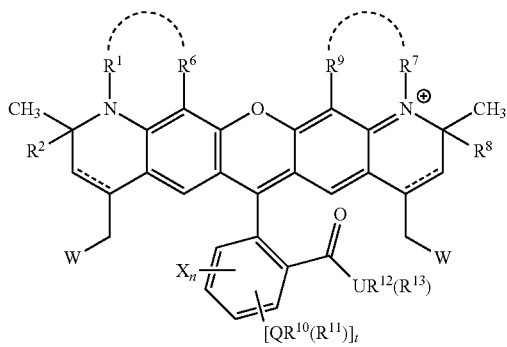

IIa

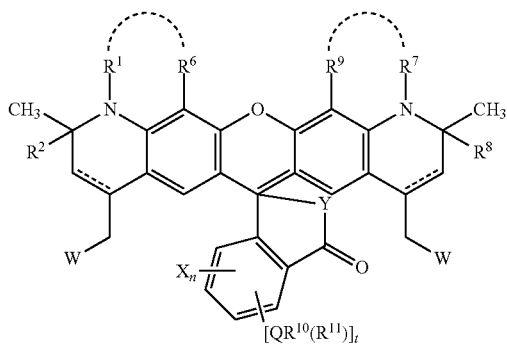

IIb wherein $R^1$, $R^7$, $R^{10}$, $R^{11}$, $R^{12}$ and $R^{13}$ independently denote H, CH$_3$, C$_2$H$_5$, any other alkyl, cycloalkyl, alkenyl, alkynyl, aryl, arylalkyl, or heteroaryl group; a (functionally) substituted alkyl, cyclo-alkyl, alkenyl, alkynyl, aryl, arylalkyl, or heteroaryl group; heterosubstituted alkyl or cycloalkyl group (e.g. azacycloalkyl, azaoxacycloalkyl, oxaalkyl, (CH$_2$CH$_2$O)$_m$CH$_3$ (m=0-24); (CH$_2$)$_m$CH$_2$OP(O)Y$^1$Y$^2$, where Y$^1$ and Y$^2$ independently denote any of the following residues: OH, O(–), OR$^a$ and OR$^b$, NHR$^a$ and NHR$^b$, NR$^a$R$^b$ and NR$^c$R$^d$, OR$^a$ and NHR$^b$, OR$^a$ and NR$^b$R$^c$, NHR$^a$ and NR$^b$R$^c$); or $R^1$, $R^7$, $R^{10}$, $R^{11}$, $R^{12}$ and $R^{13}$ may represent any combination of the said groups; in particular, one or several groups from the set $R^1$, $R^7$, $R^{10}$, $R^{11}$, $R^{12}$ and $R^{13}$ may denote (CH$_2$)$_m$COOH (m=0-23) and/or the corresponding esters (CH$_2$)$_m$COOR$^a$ and/or primary amides (CH$_2$)$_m$CONHR$^a$ and/or secondary amides (CH$_2$)$_m$CONR$^c$R$^d$ (m=0-23), oligo(ethylene glycol) derivatives with a carboxylic acid group (CH$_2$CH$_2$O)$_m$CH$_2$(CH$_2$)$_n$COOH (m=0-23; n=0,1), and the corresponding esters (CH$_2$CH$_2$O)$_m$CH$_2$(CH$_2$)$_n$COOR$^a$, and/or amides (CH$_2$CH$_2$O)$_m$(CH$_2$)$_n$CONHR$^b$ and (CH$_2$CH$_2$O)$_m$(CH$_2$)$_n$CONR$^c$R$^d$ (m=0-23; n=0,1); $R^a$ and $R^b$ ($R^c$ and $R^d$) independently denote separate substituents like H, alkyl, cycloalkyl, alkenyl, e.g. allyl, alkynyl, e.g. ethynyl or propargyl, aryl, e.g. phenyl, a heterosubstituted alkyl or cycloalkyl group, e.g. azacycloalkyl, azaoxacycloalkyl, oxaalkyl, haloacetyl-aminoalkyl (XCH$_2$CONH(CH$_2$)$_m$; X=Cl, Br, I), a functionally substituted alkyl group, e.g. ω-azidoalkyl (N$_3$(CH$_2$)$_m$) or ω-(N-maleimido)alkyl, a heterocyclic residue, e.g. N-succinimidyl, heteroaryl, e.g. 4-pyridyl, (functionally) substituted aryl, e.g. perfluorophenyl, (functionally) substituted heteroaryl, e.g. 4-pyridyloxy, or $R^a$ and $R^b$ ($R^c$ and $R^d$) form a cyclic system (only in the case of secondary amides, where $R^1$ or/and $R^7$ or/and $R^{10}$ or/and $R^{11}$ or/and $R^{12}$ or/and $R^{13}$=(CH$_2$)$_m$CONR$^a$R$^b$, or (CH$_2$CH$_2$O)$_m$CONR$^a$R$^b$, or (CH$_2$)$_m$CH$_2$OP(O)(NR$^a$R$^b$)(NR$^c$R$^d$));

$R^2$ and $R^8$ are independent from each other and denote: CH$_3$, alkyl, HOCH$_2$, hydroxyalkyl, alkoxyalkyl;

$R^6$ and $R^9$ are independent from each other and denote H, F, Cl, CH$_3$, or any other alkyl group; alternatively, $R^1$ - - - $R^6$ and/or $R^7$ - - - $R^9$=—(CH$_2$)$_2$—, —(CH$_2$)$_3$—, —CH$_2$COCH$_2$—, CH$_2$[C=N(OR$^a$)]CH$_2$— or —CH$_2$(C=N—NR$^a$R$^b$)CH$_2$—, where $R^a$ and $R^b$ have been defined above;

X=H, F or Cl (n=0-4);

Q and U independently denote N, O, S (e.g. QR$^{10}$R$^{11}$=SCH$_2$CH$_2$SO$_3$(—)); alternatively, QR$^{10}$R$^{11}$ may denote N-pyridyl (quaternary pyridinium salt or C-substituted quaternary pyridinium salt), N-imidazolyl, N$^1$—R$^a$-imidazol-3-yl, with $R^a$ as defined above;

t=4, 3, 2, 1 or 0;

Y=O or diazocarbonyl [C=N(+)=N(–)]

W=OP(O)Y$^1$Y$^2$ or P(O)Y$^1$Y$^2$ where Y$^1$ and Y$^2$ independently denote any of the following residues: OH, O(–), OR$^a$ and OR$^b$, NHR$^a$ and NHR$^b$, NR$^a$R$^b$ and NR$^c$R$^d$, OR$^a$ and NHR$^b$, OR$^a$ and NR$^b$R$^c$, NHR$^a$ and NR$^b$R$^c$; and any salt of thereof;

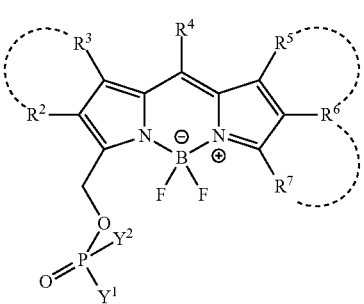

IIIa

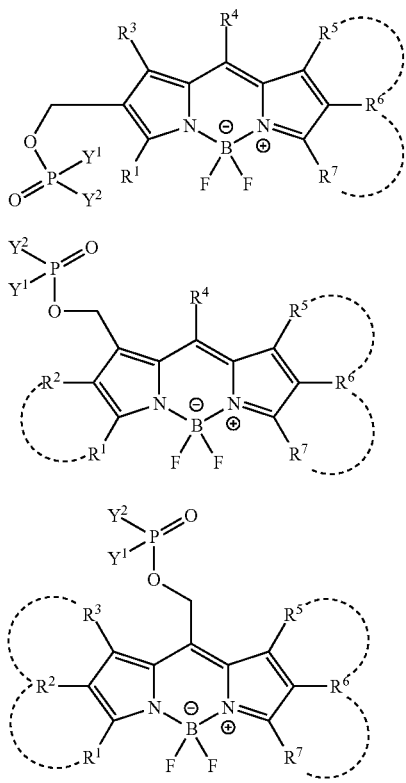

IIIb

IIIc

IIId wherein
R¹, R², R³, R⁴, R⁵, R⁶ and R⁷ independently denote H, CH₃, C₂H₅, any other alkyl, cycloalkyl, alkenyl, alkynyl, aryl, arylalkyl or heteroaryl group; (functionally) substituted alkyl, cycloalkyl, alkenyl, alkynyl, aryl, arylalkyl or heteroaryl group; heterosubstituted alkyl or cycloalkyl group (e.g. azacycloalkyl, azaoxacycloalkyl, $(CH_2)_mCH_2OP(O)Y^1Y^2$, where $Y^1$ and $Y^2$ independently denote any of the following residues: OH, O(−), $OR^a$ and $OR^b$, $NHR^a$ and $NHR^b$, $NR^aR^b$ and $NR^cR^d$, $OR^a$ and $NHR^b$, $OR^a$ and $NR^bR^c$, $NHR^a$ and $NR^bR^c$; $(CH_2CH_2O)_mCH_3$ (m=0-24)); or R¹, R², R³, R⁴, R⁵, R⁶ and R⁷ may represent the combination of the said groups, in particular one or several groups from this set may be $(CH_2)_mCOOH$ (m=0-23) and/or the corresponding esters $(CH_2)_mCOOR^a$ and/or primary amides $(CH_2)_mCONHR^a$ and/or secondary amides $(CH_2)_mCONR^cR^d$ (m=0-23), oligo(ethylene glycol) derivatives with a carboxylic acid group $(CH_2CH_2O)_mCH_2(CH_2)_mCOOH$ (m=0-23; n=0,1), and the corresponding esters $(CH_2CH_2O)_mCH_2(CH_2)_nCOOR^a$, and/or amides $(CH_2CH_2O)_m(CH_2)_nCONHR^b$ and $(CH_2CH_2O)_m(CH_2)_nCONR^cR^d$ (m=0-23; n=0,1); $R^a$ and $R^b$ ($R^c$ and $R^d$) independently denote separate substituents like H, alkyl, cycloalkyl, alkenyl, e.g. allyl, alkynyl, e.g. ethynyl or propargyl, aryl, e.g. phenyl, a heterosubstituted alkyl or cycloalkyl group, e.g. azacycloalkyl, azaoxacycloalkyl, oxaalkyl, haloacetylaminoalkyl $(XCH_2CONH(CH_2)_m$; X=Cl, Br, I), a functionally substituted alkyl group, e.g. ω-azidoalkyl $(N_3(CH_2)_m)$ or ω-(N-maleimido)alkyl, a heterocyclic residue, e.g. N-succinimidyl, heteroaryl, e.g. 4-pyridyl, (functionally) substituted aryl, e.g. perfluorophenyl, (functionally) substituted heteroaryl, e.g. 4-pyridyloxy, or $R^a$ and $R^b$ ($R^c$ and $R^d$) form a cyclic system (only in the case of secondary amides, where R¹ or/and R⁷ or/and R¹⁰ or/and R¹¹ or/and R¹² or/and $R^{13}=(CH_2)_mCONR^aR^b$, or $(CH_2CH_2O)_mCONR^aR^b$, or $(CH_2)_mCH_2OP(O)(NR^aR^b)(NR^cR^d))$;
$Y^1$ and $Y^2$ independently denote any of the following residues: OH, O(−), $OR^a$ and $OR^b$, $NHR^a$ and $NHR^b$, $NR^aR^b$ and $NR^cR^d$, $OR^a$ and $NHR^b$, $OR^a$ and $NR^bR^c$, $NHR^a$ and $NR^bR^c$; and any salt thereof.

The term "substituted" as used herein, refers to the presence of one or more substituents, in particular substituents selected from the group comprising alkyl, e.g. methyl, ethyl, propyl, butyl; isoalkyl, e.g. isopropyl, isobutyl (2-methylpropyl); secondary alkyl group, e.g. sec-butyl (but-2-yl); tert-alkyl group, e.g. tert-butyl (2-methylpropyl); cycloalkyl group, e.g. cyclopropyl, cyclobutyl, cyclopentyl, cyclohexyl; crown ether residues, e.g. 18-crown-5, 18-crown-6, crown ether residues with annelated cyclohexyl or phenyl groups, e.g. dibenzo-18-crown-6, bicycloalkyl group, e.g. bicyclo[1.1.1]but-1-yl, trialkylsilyl groups, e.g. trimethylsilyl, triethylsilyl, oligo(ethylene glycol) residues $H(CH_2CH_2O)n$ (n=2-24), e.g. $CH_3CH_2OCH_2CH_2O$; alkoxy groups, e.g. methoxy, ethoxy, isopropoxy, tert-butoxy; dialkylamino groups, e.g. dimethylamino, pyrrolidin-1-yl, piperidin-1-yl; positively charged trialkylammonio groups, e.g. trimethylammonio group $[(CH_3)_3N(+)-]$.

The term "functionally substituted" as used herein, refers to the presence of one or more functional groups, in particular including cycloalkenyl, alkenyl, e.g. ethenyl (vinyl), allyl, propen-1-yl, propen-2-yl, 1,3-butadien-1-yl, 1,3-budadien-2-yl, 1,2-propadien-1-yl (allenyl), alkynyl, e.g. ethynyl, propynyl, propargyl, aryl, e.g. phenyl, 1-naphthyl, 2-naphthyl, 9-anthracenyl-, pyren-1-yl, pyren-2-yl; one or more halogen atoms (F, Cl, Br, I), azido groups (—N₃), nitroso groups (N=O), diazo groups [=N(+)=N(−)], diazocarbonyl groups [>C=N(+)=N(−)], hydroxy groups (OH), protected hydroxy groups (OR, R=acyl, e. g. formyl, acetyl, tetrahydropyranyl, t-butyl, allyl, propargyl, phenyl, p-chlorophenyl, p-methoxyphenyl, p-nitrophenyl, perfluorophenyl, perchlorophenyl, benzyl, 2-picolyl, 4-picolyl, diphenylmethyl, triphenylmethyl, trialkylsilyl, triphenylsilyl, diphenylalkylsilyl), thiol groups (SH), protected thiol groups (SR, R was defined above), primary and secondary amino groups (NH₂ and NHR, R was defined above), hydrazo groups (—NHNH₂), hydroxylamino groups (—NHOH and H₂NO—), carbonyl groups in aldehydes and ketones (—CHO and >C=O), protected carbonyl groups (>C(OCH₃)₂, >C(OCH₂CH₂O), and other acetals and ketals), hydrazones (C=NNR'R"), oximes (>C=N—OR), thioketones (>C=S), sulfoxides (>S=O), sulfones (—SO₂—), sulfonic acid residues and their salts [—SO₃H and —SO₃(−)], carboxylic acid groups (COOH), and ester groups (COOR, R=alkyl, e. g. CH₃, C₂H₅, t-butyl; allyl, propargyl, phenyl, p-chlorophenyl, p-methoxyphenyl, p-nitrophenyl, perfluorophenyl, perchlorophenyl, benzyl, 2-picolyl, 4-picolyl, diphenylmethyl, triphenylmethyl, trialkylsilyl, triphenylsilyl, diphenylalkylsilyl, in particular, N-hydroxysuccinimidyl); primary, secondary and tertiary amido groups, phosphorodiamidite group [—OP(NR₂)₂, R=CH₃, C₂H₅, isopropyl, allyl, tert-butyl, phenyl], phosphoroamidite group [—OP(NR'₂)(OR"), R'=CH₃, C₂H₅, isopropyl, allyl, tert-butyl, phenyl, R"=H, alkyl, aryl, hetaryl], phosphorodiamidite group [—OP(NR₂), R=CH₃, C₂H₅, isopropyl, allyl, tert-butyl, phenyl], phosphoric acid residues [—OP(O)(OR')(OR"), R'(R")=H, CH₃, C₂H₅, allyl, tert-butyl, phenyl, NH₂], phosphonic acid residues [—P(O)(OR')(OR"), R'(R")=H, CH₃, C₂H₅, allyl, tert-butyl, phenyl, NH₂], N-phthalimido group. The term "functionally substituted" as used herein, also refers to the optional presence of one or more heterocyclic residues, in particular including oxirane, aziridine, thiirane, azetidine, pyrrolidine, tetrahydropyrane, tetrahydrothiophene, 1,3-oxazoline, 1,3-oxazolidine, thiophene, furane, pyrrole, pyridine, quinoline, pyrimidine, pyrimidin-4-one, pyrimidin-2-one, pyridazine, pyrazine, 1,3,5-triazine, 1,2,4-triazine, 1,3-imidazol, thiazole, 1,2,4-triazole, 1,2,3-triazole, 1,3-oxazole. The said heterocycles may be attached to the carbon framework of the substituents via various positions (e.g. 1-aziridinyl, 2-aziridinyl, pyrrolidin-1-yl, pyrrolidine-2-yl, pyrrolidin-3-yl, thiophen-2-yl, thiophen-3-yl, pyridin-2-yl, pyridin-3-yl, pyridin-4-yl, etc.). The term "functionally substituted", as used herein, also refers to the optional presence of any combination of the said functional groups with each other (e.g., 2-diazoketone groups as represented by: —COCN$_2$—). The term "functionally substituted", as used herein, also refers to the optional presence of any combination of the said functional groups with any heterocyclic residues named above.

Compounds of the general structural formulae Ia, b above are coumarin dyes, compounds of the formulae IIa, IIb above are rhodamine dyes and the compounds of the formulae IIIa-d above are BODIPY dyes.

These dyes may contain O-phosphorylated methyl groups (W=OP(O)(OH)$_2$) or C-phosphorylated (W=P(O)(OH)$_2$) methyl groups (phosphonic acid residues), as well as the derivatives of the said groups. Compounds IIb represent a specific embodiment of the invention. They are the derivatives of 9H-xanthenes in the so-called "closed form" possessing the spiro-carbon atom bound with oxygen (Y=O) or diazocarbonyl group (Y=C=N$_2$), preferably with hydroxylated methyl groups, or phosphorylated hydroxymethyl residues.

The novel fluorescent dyes of the present invention exhibit a number of favorable characteristics:

a) excitation with light sources in the range from 405 nm to 633-650 nm;
b) emission of light in the range from 520 nm to 700 nm;
c) providing easy detection due to high fluorescence quantum yields, especially in aqueous solutions and after bioconjugation;
d) high photostability, especially with intensive red light, e.g. under STED conditions (by depletion with very strong light; preferably at 592 or 750 nm), particularly in the presence of air-oxygen;
e) possibility to use coumarin dyes with large Stokes shifts for two- and multicolour imaging, in combination with other fluorescent dyes possessing smaller Stokes shifts;
f) diffraction unlimited optical resolution in far-field microscopy and its combinations with other techniques (e.g. fluorescence correlation spectroscopy, fluorescence lifetime imaging (FLIM), fluorescent resonance energy transfer (FRET), fluorescence recovery after photobleaching (FRAP), and others).

According to preferred embodiments of the present invention, the substituents in the above formulae Ia,b are defined as follows:

$R^1$=an acid group $(CH_2)_m COOH$ (m=1-6) or an (active) ester $(CH_2)_m COOR^a$ ($R^a$=heterocyclic residue, e.g., N-succinimidyl, 4-pyridyl, benzotriazol-1-yl; or $R^a$=(substituted) aryl group, e.g. pentachlorophenyl, pentafluorophenyl, 2,3,5,6-tetrafluorophenyl, etc.); as well as primary amides $(CH_2)_m CONHR^a$ (m=1-6, $R^a$=$(CH_2)_m$—N-maleimido group, $(CH_2)_m$—N$_3$, $(CH_2)_m$—NHCOCH$_2$X (X=Br, I), $(CH_2)_m$—NHCO-[the residue of any natural compound, e. g. biotin, ryanodin, phalloidin, any protein, carbohydrate, etc.]); oligo(ethylene glycol) derivatives with a carboxylic acid group $(CH_2CH_2O)_m CH_2(CH_2)_n COOH$ (m=0-12; n=0, 1), and the corresponding esters $(CH_2CH_2O)_m CH_2(CH_2)_n COOR^a$, as well as primary amides $(CH_2CH_2O)_m CH_2 (CH_2)_n CONHR^a$ (m=0-12; n=0,1, $R^a$ as defined above)

$R^2$=CH$_3$, or CH$_2$OH $R^3$ and $R^6$=H, or $R^1$ - - - $R^6$=—(CH$_2$)$_3$—

$R^4$=H, CH$_3$ $R^5$=heteroaryl, e.g. 2-pyridyl, 4-pyridyl, pyrimidin-2-yl, pyrimidin-3-yl, pyrimidin-4-yl, pyrazin-2-yl, pyridazin-3-yl, pyridazin-4-yl, 1,3,5-triazinyl, 1,2,4-triazin-3-yl; CF$_3$, CN, C≡CR$^a$ (R$^a$=aryl, e.g. phenyl, heteroaryl, e.g. 2-pyridyl, 4-pyridyl, pyrimidin-2-yl, pyrimidin-3-yl, pyrimidin-4-yl, pyrazin-2-yl, pyridazin-3-yl, pyridazin-4-yl, 1,3,5-triazinyl, 1,2,4-triazin-3-yl W=OP(O)(OH)$_2$ or P(O)(OH)$_2$, and any salt thereof.

Especially preferred compounds of the structural formulae Ia,b above have one of the following formulae:

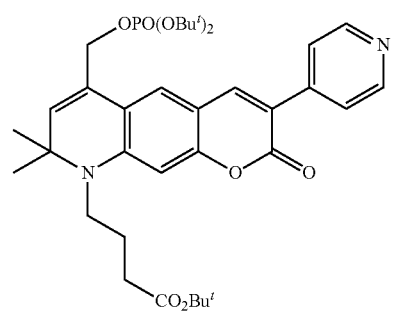

10

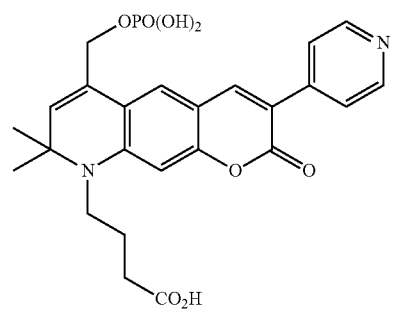

11

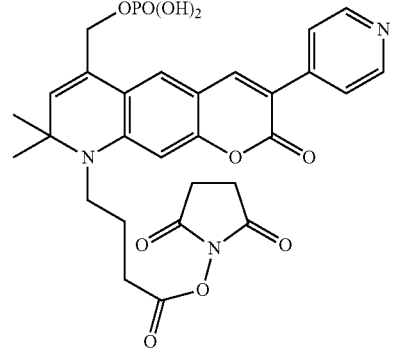

12

-continued

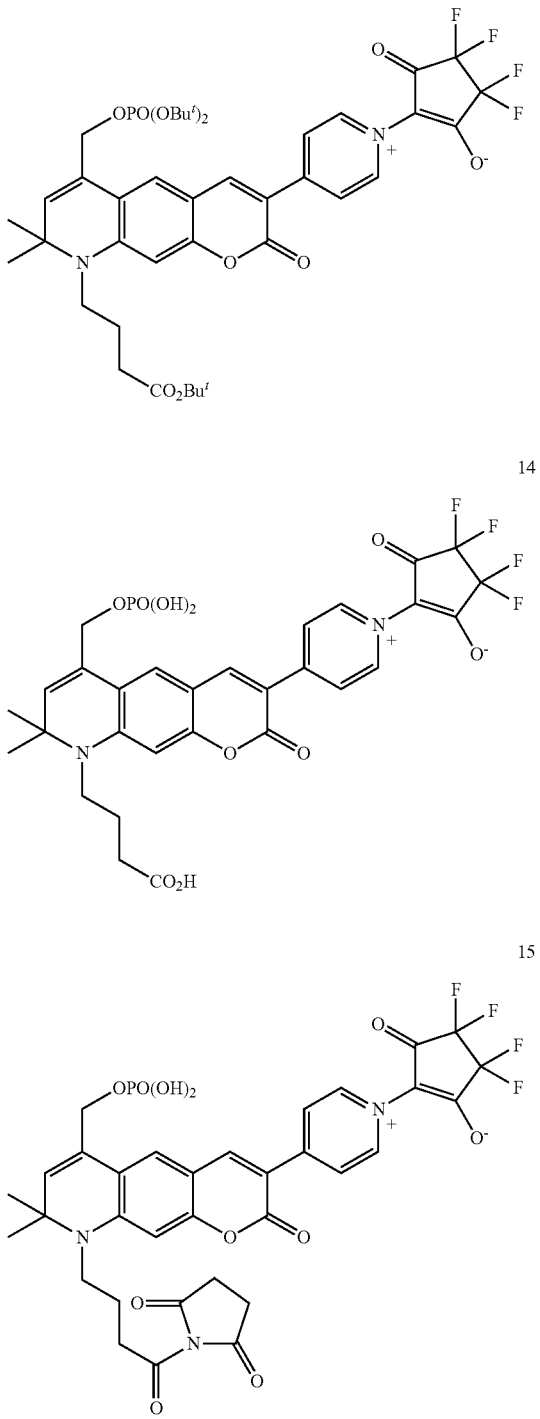

According to preferred embodiments of the invention, the substituents in the above formulae IIa,b are defined as follows:

$R^1$=H, $CH_3$, $C_2H_5$, $(CH_2CH_2O)_mCH_3$, $(CH_2CH_2O)_mC_2H_5$, (m=2-12), or $R^1$ - - - $R^6$=$(CH_2)_3$—

$R^2$=$CH_3$, $CH_2OH$ $R^6$=H, or $R^1$ - - - $R^6$=—$(CH_2)_3$—

$R^7$=H, $CH_3$, $C_2H_5$, $(CH_2CH_2O)_mCH_3$, $(CH_2CH_2O)_mC_2H_5$, (m=2-12) or $R^7$ - - - $R^9$=—$(CH_2)_3$—

$R^8$=$CH_3$, $CH_2OH$ $R^9$=H, or $R^7$ - - - $R^9$=—$(CH_2)_3$—

$R^{10}$=H (or absent)

$R^{11}$=$CH_2CH_2SO_3(-)$; $(CH_2)_mCOOH$ (m=1-6) or an (active) ester $(CH_2)_mCOOR^a$ ($R^a$=heterocyclic residue, e. g., N-succinimidyl, 4-pyridyl, benzotriazol-1-yl; or $R^a$=(substituted) aryl group, e.g., pentachlorophenyl, pentafluorophenyl, 2,3,5,6-tetrafluoro-phenyl, etc.); as well as primary amides $(CH_2)_mCONHR^a$ (m=1-6, $R^a$=$(CH_2)_m$—N-maleimido group, $(CH_2)_m$—$N_3$, $(CH_2)_m$—$NHCOCH_2X$ (X=Br, I), $(CH_2)_m$—NHCO-[the residue of any natural compound, e. g. biotin, ryanodin, phalloidin, any protein, carbohydrate, etc.]); oligo(ethylene glycol) derivatives with a carboxylic acid group $(CH_2CH_2O)_mCH_2(CH_2)_n$COOH (m=0-12; n=0,1), and the corresponding esters $(CH_2CH_2O)_mCH_2(CH_2)_nCOOR^a$, as well as primary amides $(CH_2CH_2O)_mCH_2(CH_2)_nCONHR^a$ (m=0-12; n=0, 1, $R^a$ as defined above) CH2CH2SO3(-)

$R^{12}$=H, $CH_3$ (or absent)

$R^{13}$=H, $(CH_2)_mCOOH$ (m=1-6) or an (active) ester $(CH_2)_m$COOR$^a$ ($R^a$=heterocyclic residue, e.g. N-succinimidyl, 4-pyridyl, benzotriazol-1-yl; or $R^a$=(substituted) aryl group, e.g. pentachlorophenyl, pentafluorophenyl, 2,3,5,6-tetrafluorophenyl, etc.); as well as primary amides $(CH_2)_m$CONHR$^a$ (m=1-6, $R^a$=$(CH_2)_m$—N-maleimido group, $(CH_2)_m$—$N_3$, $(CH_2)_m$—$NHCOCH_2X$ (X=Br, I), $(CH_2)_m$—NHCO-[the residue of any natural compound, e. g. biotin, ryanodin, phalloidin, any protein, carbohydrate, etc.]); oligo(ethylene glycol) derivatives with a carboxylic acid group $(CH_2CH_2O)_mCH_2(CH_2)_n$COOH (m=0-12; n=0,1), and the corresponding esters $(CH_2CH_2O)_mCH_2$$(CH_2)_n$COOR$^a$, as well as primary amides $(CH_2CH_2O)_m$$CH_2(CH_2)_n$CONHR$^a$ (m=0-12; n=0,1, $R^a$ as defined above)

Q=N, S

U=O, N

X=F, Cl

Y=O, C=N(+)=N(-)

W=OP(O)(OH)$_2$ or P(O)(OH)$_2$, and any salt thereof.

Especially preferred compounds of the structural formulae IIa,b above have one of the following formulae:

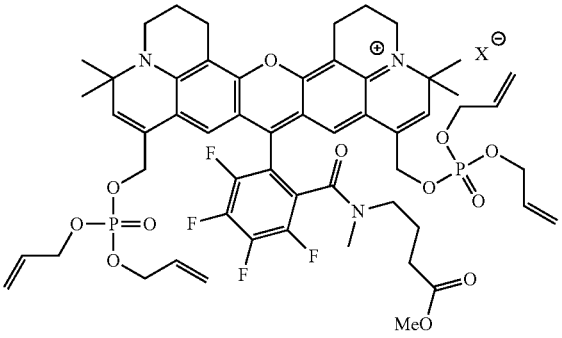

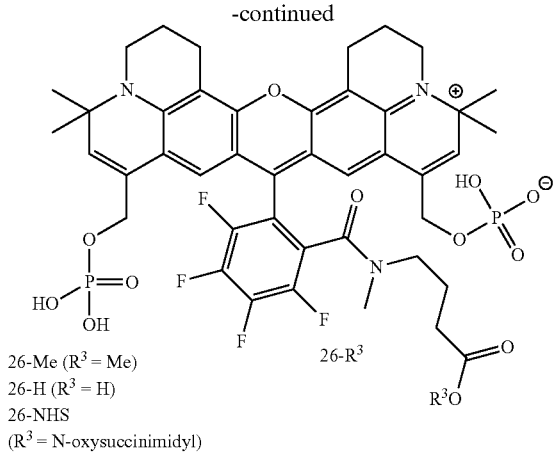

26-Me (R³ = Me)
26-H (R³ = H)
26-NHS
(R³ = N-oxysuccinimidyl)

According to preferred embodiments of the invention, the substituents in the above formulae IIIa-d are defined as follows:

$R^1$=alkyl (CH$_3$, C$_2$H$_5$), functionally substituted alkyl (HOOCCH$_2$CH$_2$—); aryl (phenyl, p-methoxyphenyl), (functionally) substituted aryl (p-HOOCCH$_2$OC$_6$H$_4$CH=CH—, p-HOOCCH$_2$OC$_6$H$_4$—), C$_6$H$_5$—(CH=CH)$_n$— (n=1, 2); C$_6$H$_5$—C≡C—; heteroaryl (e.g. thiophen-2-yl, pyrrol-2-yl)

$R^2$=H, alkyl (CH$_3$, C$_2$H$_5$)

$R^3$=H, alkyl (CH$_3$, C$_2$H$_5$), phenyl $R^4$=H, alkyl (CH$_3$, C$_2$H$_5$), CF$_3$, functionally substituted alkyl (HOOCCH$_2$CH$_2$—, N$_3$(CH$_2$)$_n$, n=2-6); aryl (phenyl), (functionally) substituted aryl (p-MeOC$_6$H$_4$, p-HOC$_6$H$_4$, p-HOOCC$_6$H$_4$), aryl-(CH=CH)$_n$— (n=1, 2); aryl-C≡C—

$R^5$=$R^3$=H, alkyl (CH$_3$, C$_2$H$_5$), phenyl $R^6$=H, alkyl (CH$_3$, C$_2$H$_5$)

$R^7$=alkyl (CH$_3$, C$_2$H$_5$), functionally substituted alkyl (HOOCCH$_2$CH$_2$); aryl (phenyl, p-methoxyphenyl), (functionally) substituted aryl (p-HOOCCH$_2$OC$_6$H$_4$CH=CH—, p-HOOCCH$_2$OC$_6$H$_4$—), C$_6$H$_5$—(CH=CH)$_n$— (n=1, 2); C$_6$H$_5$—C≡C—; hetaryl (e.g. thiophen-2-yl, pyrrol-2-yl)

Y1, Y2=OH or any salts.

A further aspect of the present invention relates to a method for preparing a fluorescent dye according to general formulae Ia-Ib and IIa-IIB of claim 1, comprising a) providing a precursor compound wherein W in formulae Ia-Ib and IIa-IIb of claim 1 above is replaced by a reactive group W' selected from the group consisting of halogen (Cl, Br, I), hydroxy (OH), ether (preferably aryl ether), acyloxy (OCOR), or sulfonyloxy (OSO$_2$R) residues;

b) reacting said group W' of the precursor compound with a phosphorylating agent to obtain a compound of the general formulae Ia-Ib and IIa-IIb of claim 1;

c) optionally performing post-synthetic modifications of the (protected) phosphate group.

In more specific embodiments of the invention, step c) comprises the deprotection of the tertiary phosphate ester with two equal groups (allyl, benzyl, phenyl, t-butyl, etc.) to obtain the target compound with a primary phosphate group or, alternatively, saponification of the tertiary phosphate group to obtain the secondary phosphate group; and, optionally, amidation of the primary or secondary phosphate group in the presence of an amine and the coupling reagent (e.g. N,N'-substituted carbodiimide) to obtain the functionally substituted amide (or amido ester) of the target phosphoric acid.

The present invention also provides precursor compounds and building blocks for synthesizing the dyes of formulae Ia,b and IIa,b above.

In particular, in a closely related aspect the present invention provides a precursor compound for preparing a fluorescent dye of the general formulae Ia-Ib and IIa-IIb according to the method disclosed above, having one of the general formulae Ia-Ib and IIa-IIb of claim 1 but wherein W in said formulae Ia-Ib and IIa-IIb is replaced by a reactive group W' selected from the group consisting of halogen (Cl, Br, I), hydroxy (OH), ether (preferably aryl ether), acyloxy (OCOR), or sulfonyloxy (OSO$_2$R) residues.

In one specific embodiment of the invention, the precursor compounds have one of the following formulae:

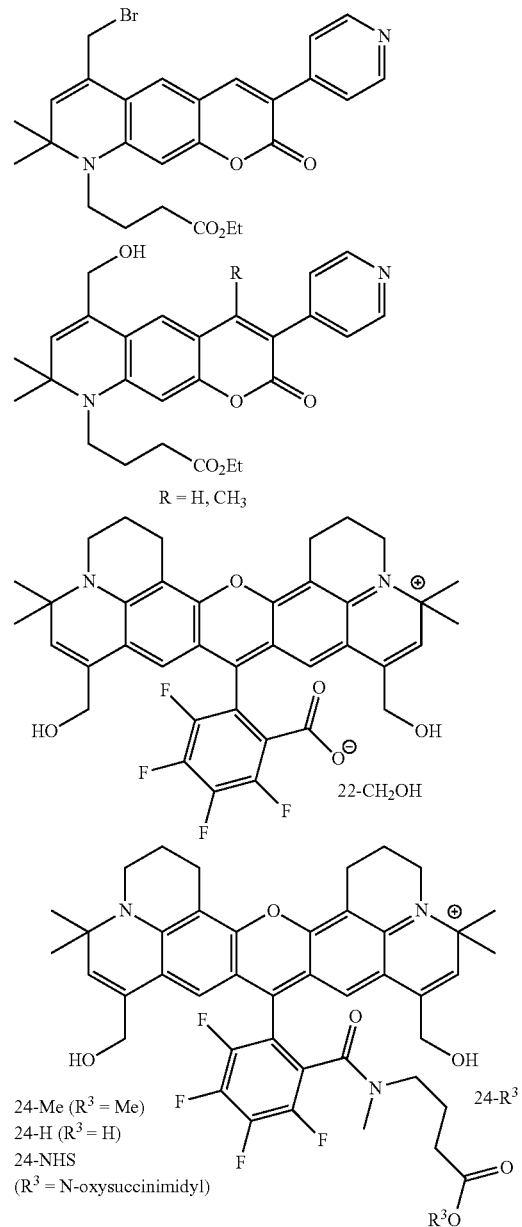

R = H, CH$_3$

22-CH$_2$OH

24-Me (R³ = Me)
24-H (R³ = H)
24-NHS
(R³ = N-oxysuccinimidyl)

Synthesis of Universal Precursors; Principles of Construction of the Fluorescent Dyes with Hydroxymethyl Groups and Phosphoric Acid Residues Phosphorylated Coumarins Synthesis and properties of hydrophilic coumarins decorated with sulfonic acid groups have been disclosed [P. Czerney, M. Wenzel, B. Schwender, F. Lehmann, U.S. Pat. No. 7,563,907 B2, 21 Sep. 2009; A. Zilles, J. Arden-Jacob, K.-H. Drexhage, N. U. Kemnitzer, M. Hamers-Schneider US 2006/0179585 A1, WO2005/003086 A2]. Introduction of the sulfonic acid residue into the methyl group at C-4 in 2,2,4-trimethyl-1,2-dihydroquinolines—precursors to hydrophilic coumarins with large Stokes shifts—is performed in concentrated sulfuric acid or even oleum (solution of $SO_3$ in $H_2SO_4$). These harsh conditions are also required for the preparation of sulfonated rhodamines (xanthenes) [F. Mao, W.-Y. Leung, R. P. Haugland, U.S. Pat. No. 6,130,101, 10 Oct. 2000]. Though this approach provides the required hydrophilic precursors or the fluorescent dyes themselves, the severe reaction conditions are incompatible with several important functional groups which do not tolerate concentrated sulfuric acid (e.g. tert-butyl ethers, esters and carbamates, diazo groups, and many other functional groups). In this respect, the synthetic route to the hydrophilic fluorescent dyes of the invention is advantageous, as it provides the phosphorylated coumarins and rhodamines prepared under mild conditions.

Preparation of the useful building blocks 9a-d for the synthesis of various coumarines dyes emitting in the green and red spectral regions is exemplified in Scheme 1. The selective protection of the hydroxy-group in m-aminophenol was carried out as described in the literature [N. Senda, A. Momotake, Y. Nishimura, T. Arai, *Bull. Chem Soc. Jpn.* 2006, 79, 1753-1757]. The Skraup condensation was performed in the presence of ytterbium (III) triflate [M.-E. Theocliton and L. A. Robinson, *Tetrahedron Letters* 2002, 43, 3907-3910] and provided the precursor 3 with the 1,2-dihydroquinoline moiety in good yield. The alkylation of compound 3 with t-butyl 3-iodobutyrate in the presence of Hönig base afforded ester 4. Oxidation of the methyl group at the position 4 was achieved by a standard procedure with selenium dioxide. The reduction of aldehyde 5 into alcohol 6a proceeded smoothly with sodium borohydride. The phosphorylation of alcohol 6a was performed as described in the literature [e. g., a) G. G. Durgam, T. Virag, M. D. Walker, R. Tsukahara, S. Yasuda, K. Liliom, L. A. van Meeteren, W. H. Moolenaar, N. Wilke, W. Siess, G. Tigyi, D. D. Miller, *J. Med. Chem.* 2005, 48, 4919-4930; b) J. W. Perich, R. B. Johns, *Synthesis* 1988 (2), 142-144]. The required compound 7a with the protected phosphoric acid residue was obtained in 21% yield (over two steps). Alkohol 6a can easily be converted into bromide 7b (e.g. with triphenylphosphine-bromine complex in the presence of pyridine or imidazole in dichloromethane or THF). The Arbuzov reaction of 7b can be used for the preparation of the C-phosphorylated compound 7c. Desilylation of the phenolic hydroxyl in compounds 7a,c using TBAF led to phenols 8a,c. Hydrogenation of the double bond in compounds 8a,c affords phenols 8b,d with 1,2,3,4-tetrahydroquinoline framework, respectively. Carbonylation of phenols 8a-d with Vilsmeyer reagent resulted in the target compounds 9a-d (Scheme 1). Aldehydes 9a,b and 9b,c represent aromatic aldehydes with 2-hydroxy group.

Scheme 1. Preparation of the building blocks 9a, b.

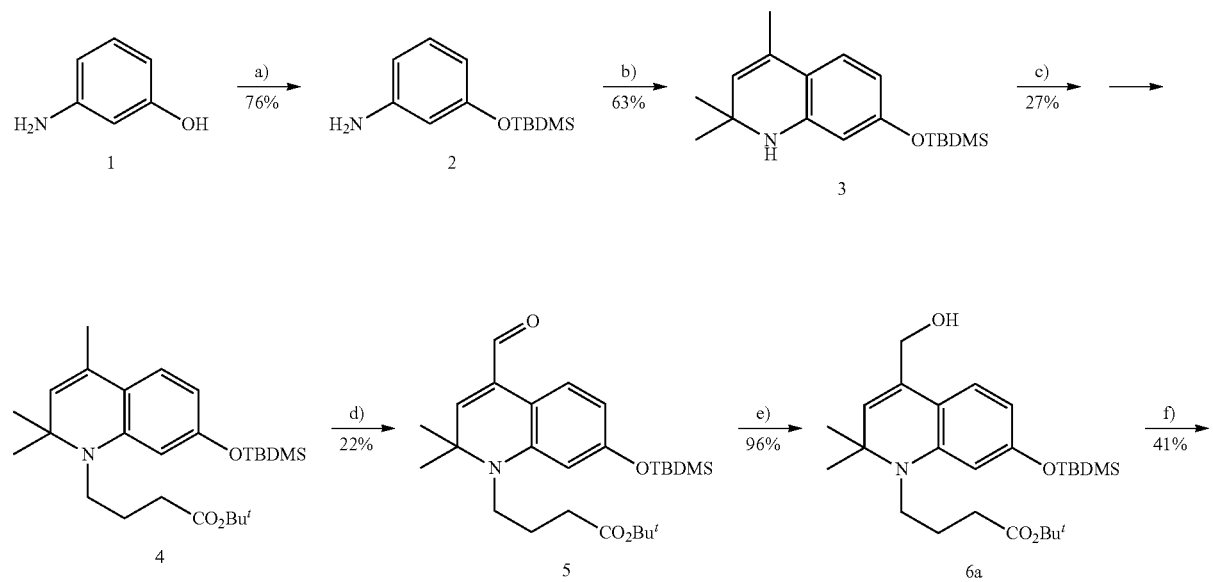

-continued

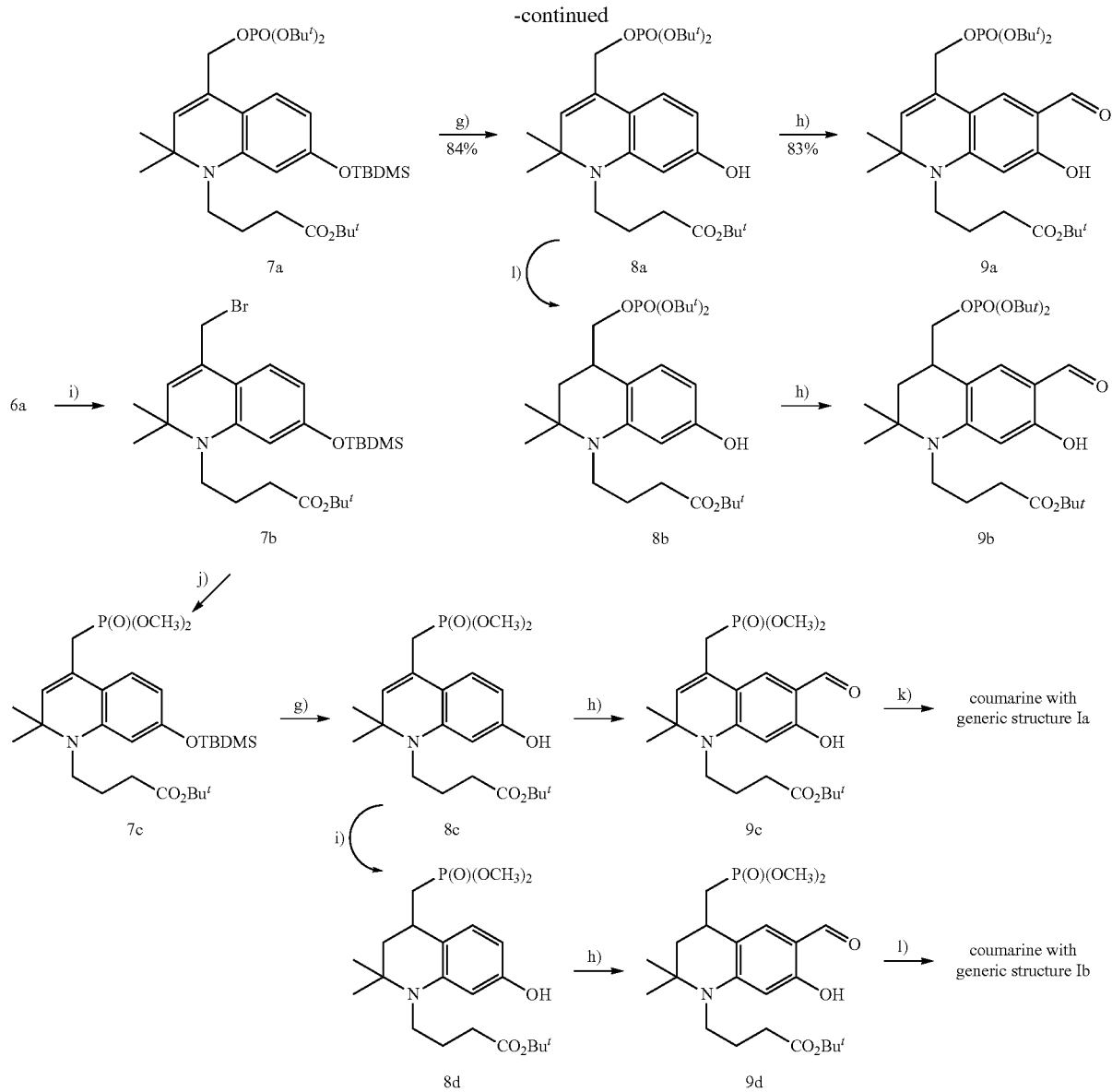

Reagents and conditions: a) TBDMSCl, Im/DMF, RT, 1 h; +55° C., 0.5 h; b) acetone, Yb(OTf)$_3$/RT, 16 h; c) t-butyl 4-iodobutyrate, iPr$_2$NEt/+110° C., 4 days; d) SeO$_2$/dioxane, +60° C., 1 h; e) NaBH$_4$/THF, MeOH, RT, 5 min; f) iPr$_2$NP(OBu$^t$)$_2$, 1H-tetrazole/THF, +40° C., 1 h; then MCPBA/+5° C., 5 min; g) TBAF•3H$_2$O/THF, +5° C., 5 min; h) POCl$_3$, DMF/+5° C., 4 h; +50° C., 15 min; i) Br$_2$/Ph$_3$P, pyridine, CH$_2$Cl$_2$, 0° C.; then 6a, 0° C. ... RT; j) (CH$_3$O)$_3$P, 170° C.; k) ArCH$_2$COOH, DCC, NEt$_3$, DMAP/dichloromethane, RT, 16 h; l) H$_2$, Pd/c, dioxane or ethyl acetate.

Compounds 9a,b can readily be used by chemists skilled in the art for the synthesis of coumarin dyes with generic structures Ia and Ib (R$^2$=Me). For example, according to the approach exemplified in Scheme 2, the condensation reaction of 9a,b with the α-substituted acetic acid derivatives directly affords coumarins. [Cf.: S. H. Mashraqui, D. Vashi, H. D. Mistry Synth. Comm. 2004, 34, 3129-3134] In particular, the reaction of aldehyde 9a with 4-pyridyl acetic acid provided coumarin 10 in one step and under mild conditions (Scheme 2). Deprotection of the t-Bu ester 10 with trifluoroacetic acid (TFA) led to compound 11 in high yield (93%). In this case, both acidic groups—phosphoric and carboxylic—were deblocked simultaneously, because both of them were protected as t-butyl esters. Coumarins prepared from compounds 9c,d require two separate deprotection steps: a strong acid (e.g. TFA or HCl) for t-butyl carboxylate deprotection and trimethylsilyl bromide in an organic solvent (e.g. dichloromethane or acetonitrile) for the liberation of the free phosphonic acid from the dimethyl phosphonate. The deprotected carboxylic acid (e.g. compound 11), can be used in various (bio)conjugation procedures. For instance, the corresponding aminoreactive N-succinimidyl ester 12 was prepared from acid 11 using HATU as the coupling reagent.

Furthermore, dyes with an emission in the red region can be obtained by decreasing the electron density in the heterocyclic ring at the 3-position of the coumarin chromophore (e.g., transforming the pyridine ring to a pyridinium salt by quaternization of the nitrogen atom). For example, the reaction of the green dye 10 with perfluorocyclopentene provided compound 13 emitting red light. Deprotection of all acidic groups in compound 13 (carboxylic and phosphoric acids) was achieved in 90% yield. The usefulness of acids 11 and 14 is illustrated by the efficient preparation of NHS esters 12 and 15, in which only the carboxylic groups were activated, while the phosphoric acid residues were kept free.

ane to a mixture of alcohol 22-CH$_2$OH and the corresponding aldehyde 22-CHO (Scheme 3). The aldehyde 22-CHO was reduced with sodium borohydride to the alcohol 22-CH$_2$OH

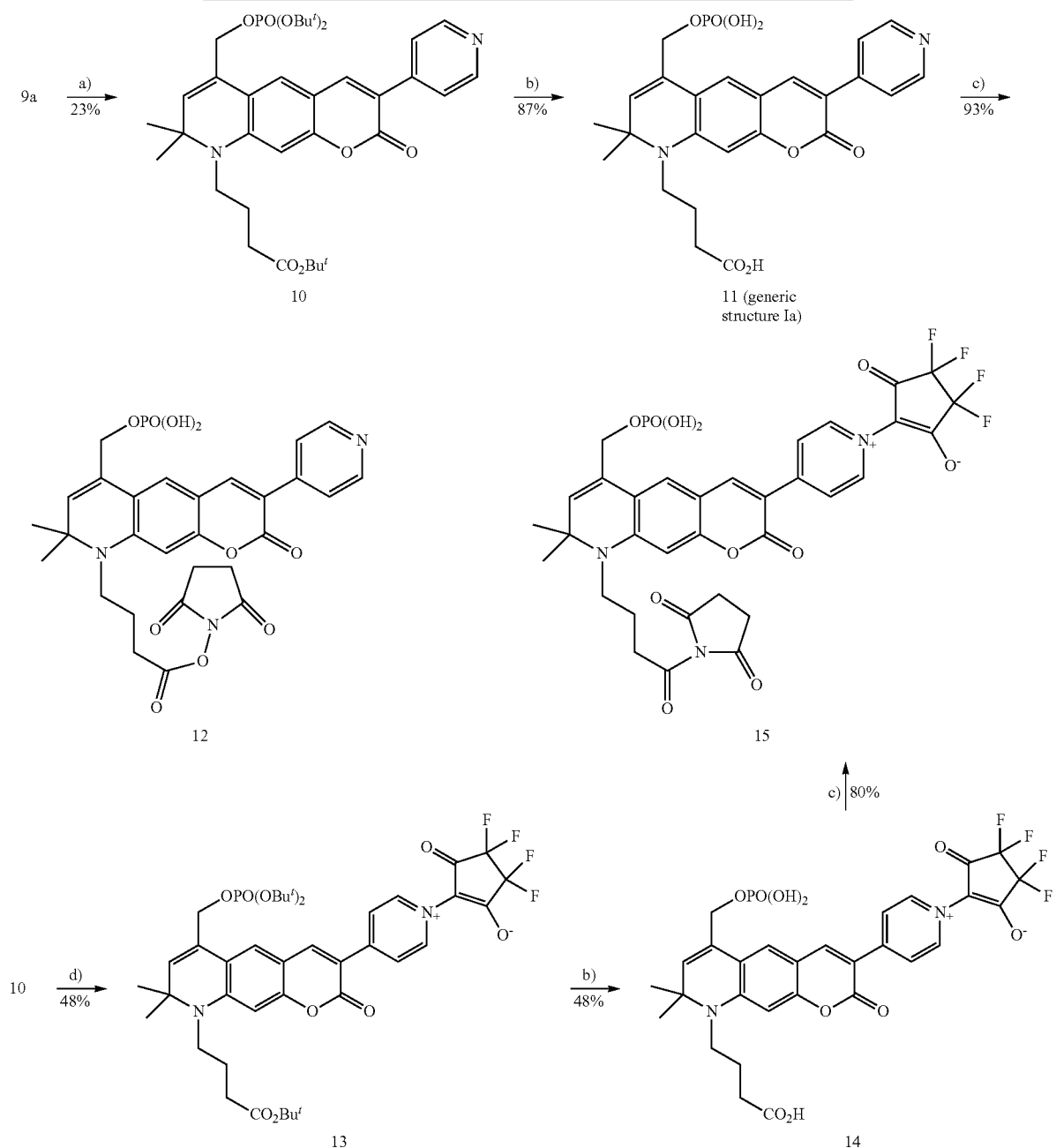

Scheme 2. Assembly of the phosphorylated coumarin dyes 11 and 14 from the building block 9a.

Reagents and conditions: a) 4-pyridylacetic acid, DCC, NEt$_3$, DMAP/dichloromethane, RT, 16 h; b) trifluoroacetic acid/RT, 4 h; c) N-hydroxysuccinimide, HATU, NEt$_3$/dichloromethane, RT, 16 h; d) perfluorocyclopentene/EtOH, H$_2$O, + 60° C., 3 h.

Hydroxylated and Phosphorylated Rhodamine Dyes

The starting rhodamine dye 21 was prepared according to the recipe described in U.S. Pat. No. 6,372,907 and the procedure reported by K. Kolmakov et. al [K. Kolmakov, V. N. Belay, J. Bierwagen, C. Ringemann, V. Müller, C. Eggeling, S. W. Hell, *Chem. European Journal*, 2010, 16, 158-166]. The two methyl groups in compound 21 were directly oxidized at the allylic positions with selenium dioxide in aqueous dioxane in a one-pot fashion. Amidation of rhodamine 22-CH$_2$OH was carried out with methyl N-methyl-W-aminobutyrate in the presence of 2-(1H-7-azabenzotriazol-1-yl)-1,1,3,3-tetramethyl uronium hexa-fluorophosphate (HATU), as illustrated in Scheme 3. The protection of the hydroxy groups in 22-CH$_2$OH for this reaction was unnecessary. Methyl N-methyl-ω-aminobutyrate 23-H (see Scheme 3) was prepared by deprotection of its Z-derivative (23-Z), which itself was synthesized from commercially available Z-ω-aminobutyric acid by methylation [V. P. Boyarskiy, V. N. Belay, R. Medda, B. Hein, M. Bossi, S. W. Hell, *Chem. Eur. J.* 2008, 14, 1784-1792]. In order to prevent the cyclization of compound 23-H into N-methyl-γ-butyrolactame (also known as N-methylpyrrolidone, NMP), it is important to carry out the hydrogenolytic cleavage of N-benzyloxycarbonyl protecting group in the presence of a strong acid (e.g. HCl). However, under basic conditions, the amidation of the amino ester 23-H by the activated carboxylic group of the zwitterionic dye 22-CH$_2$OH was found to proceed faster than the cyclization of 23-H to the five-membered amide (NMP). Rhodamine 24-Me was phosphorylated at both OH-sites (Scheme 3) by reaction with the commercially available diallyl N,N-diisopropyl phosphoramidite, assisted by 2H-tetrazole, and then oxidized (one-pot) to the phosphonate 25 [for examples, see: a) W. Bannwarth, E Künig, *Tetrahedron Lett.* 1989, 30, 4219-4222, b) T. Ohnuki, T. Tsuji, S. Miyazaki, T. Moriguchi, T. Nishi, *Synlett* 2009, 910-912]. All four allyl groups were removed from bis(diallyl phosphonate) 25 in the presence of a Pd(0) catalyst [Pd(Ph$_3$P)$_4$], as it is usually performed in the case of allyl-protected carboxylic and phosphoric acids (for examples, see: a) E. J. Corey, S. Choi, *Tetrahedron Lett.* 1993, 34, 6969-6972; b) W. Bannwarth, E Künig, *Tetrahedron Lett.* 1989, 30, 4219-4222; c) Y. Hayakawa, H. Kato, M. Uchiyama, H. Kajino, R. Noyori, *J. Org. Chem.* 1986, 51, 2400-2402). The methyl ester groups in rhodamines 26-Me and 24-Me were saponificated in very dilute alkaline solution. Under these conditions, the nucleophilic aromatic substitution of fluorine atoms did not take place.

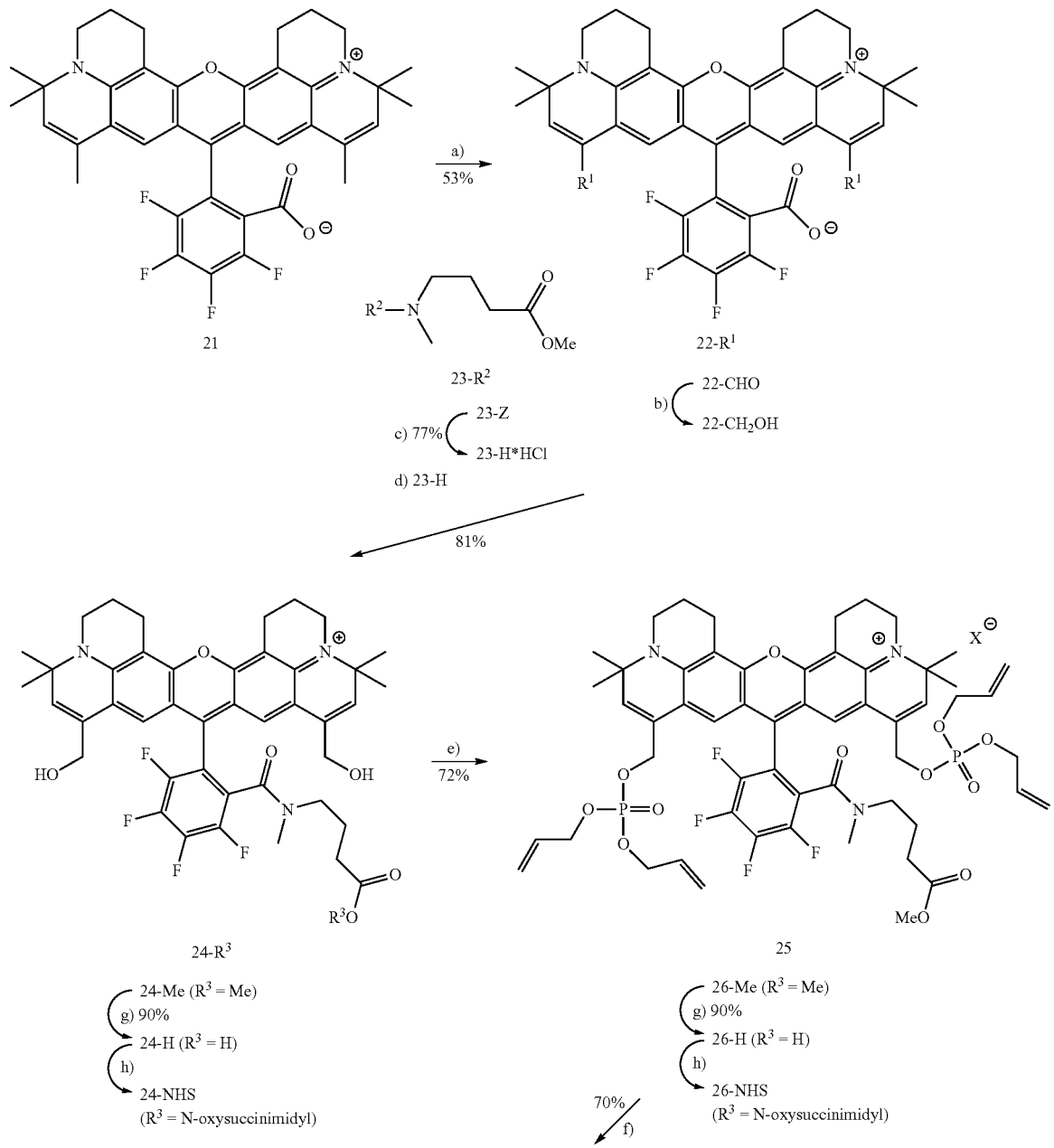

Scheme 3. Synthesis of a rhodamine dye with phosphorylated hydroxy groups (26-H).

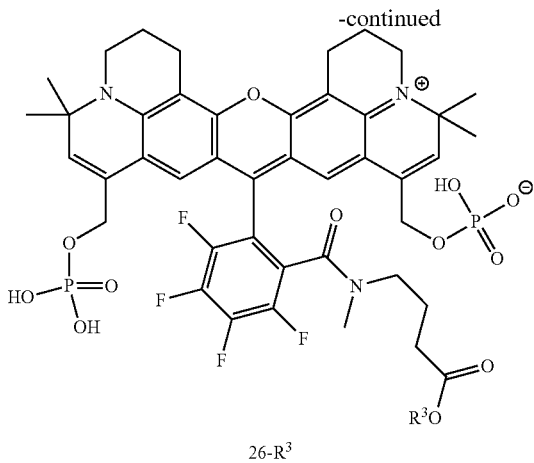

26-R³

Reagents and conditions: a) SeO₂, aq. dioxane, reflux; b) NaBH₄, EtOH, 0° C.; c) H₂, Pd/C (10% Pd), EtOH, RT; d) 2-(1H-7-azabenzotriazol-1-yl)-1,1,3,3-tetramethyl uronium hexafluorophosphate (HATU), CH₂Cl₂, CH₃CN, Et₃N, -5° C.; e) diallyl N, N-diisopropylphosphoramidite, THF, 2H-tetrazole, then t-BuOOH; f) Pd(PPh₃)₄, Et₃N*HCOOH, THF, 40° C.; g) aq. KOH, THF, RT; h) O-(N-succinimidyl)-1,1,3,3-tetramethyluronium tetrafluoro-borate (TSTU), Et₃N, DMF.

Dye 22-CH₂OH represents an important precursor which can be used by a person skilled in the art for the straightforward (yet multistep) preparation of the caged rhodamines IIb (Y=CN₂) in FIG. 1 and claim 2 (e.g. according to the recipe disclosed in WO 2011029459). Two of the four fluorine atoms in compounds 21-26 are prone to the stepwise nucleophilic substitution with amines or thiols (e.g. HSCH₂COOEt and HSCH₂CH₂SO₃Na); these transformations increase the versatility of the hydroxylated and phosphorylated rhodamines depicted in Scheme 3.

Phosphorylated BODIPY Dyes: Straightforward Syntheses from the Available Hydroxymethyl Precursors BODIPY dyes may easily be decorated with the primary phosphate group(s), because the corresponding hydroxymethyl derivatives 27a-d are readily available. For example, compounds of the type 27a have been obtained via selective side-chain oxidation of peralkylated pyrromethene-BF₂ complexes with lead(IV) tetraacetate [G. Sathyamoorthi, L. T. Wolford, A. M. Haag, J. H. Boyer, *Heteroatom. Chem.* 1994, 5, 245-249].

Scheme 4. Preparation of BODIPY dyes with phosphorylated hydroxy groups (IIIa-d) from the available hydroxymethyl derivatives (27a-d).

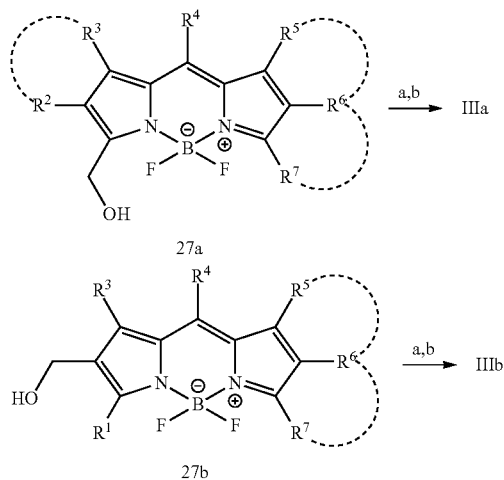

Reagents and conditions: a) diallyl N,N-diisopropylphosporamidite, THF, 2H-tetrazole, then t-BuOOH; b) Pd(PPH₃)₄, Et₃N*HCOOH, THF, 40° C.

Hydroxymethylated compounds of the type 27b and 27c have been disclosed by R. P. Haugland, H. C. Kang in U.S. Pat. No. 4,774,339, and by R. S. Brown, S. P. Tabash, I. S. Kosin, E. J.-P. Marcotte, A. N. Ley, K. R. Hall, M. Hussain, P. V. Hodson, P. Akhtar and J. G. St. Marseille in WO 2004 027084, respectively. Further, BODIPY dyes with OHCH₂-group in the meso-position (C-8) are numerous; for the recent example, see: G. Cosa, K. Krumova, *J. Am Chem. Soc.* 2010, 132, 17560-17569. The straightforward phosphorylation sequence depicted in Scheme 4 transforms these hydroxylated building blocks into the required primary phosphates IIIa-d. Oxidation of the intermediate phosphite into diallyl phosphate (the structures are not shown; for an example of a similar diallyl phosphate, see compound 25 in Scheme 3) may be achieved by a person skilled in the art not only with tBuOOH, but also with m-chloroperoxybenzoic acid, hydrogen peroxide or other oxidation agents. The intermediate diallyl phosphates may be cleaved under mild conditions with numerous reducing agents or hydrogen-donors in the presence of Pd(0)-catalysts (e. g. Pd(Ph₃P)₄ in Scheme 4, or Pd(dba)₂, or Pd₂(dba)₃*CHCl₃ with Ph₃P; dba=1,3-dibenzylideneacetone). In this respect, the allyl phosphate esters have an advantage over other alkyl phosphates (e. g. methyl or ethyl phosphates), because these deprotection conditions are compatible with the presence of various functional groups and auxochromes attached to the BODIPY fluorophore. Along with diallyl phosphates, di-(tert-butyl)phosphates $(t\text{-BuO})_2 P(O) NR_2$ (R=Et or iPr) can be used in the phosphorylation step. In this case, the deprotection has to be performed with a strong acid (e.g. trifluoroacetic or hydrochloric); under these conditions, the BODIPY dyes are know to be stable.

Scheme 4 illustrates that it is easy to attach the polar and hydrophilic primary phosphate groups(s) to the BODIPY scaffold. On the contrary, it is not so easy to introduce other classic "hydrophilizators"—like sulfonic acid residues—to the BODIPY framework. Though the BODIPY dyes are photostable, and their emission intensity does not depend to a great extent on the nature of solvent, the presence of the polar hydrophilic (phosphate) groups is advantageous, as it not only improves the solubility and resistance against photobleaching, but also prevents aggregation of the dye molecules in polar aqueous solutions. Another wide-known drawback of the BODIPY dyes is that the fluorescence signal of their bioconjugates is not directly proportional to the degree of labeling: at a certain level, an increase in the labeling degree does not improves the emission intensity any further (it may even decrease). The presence of the polar hydrophilic (phosphate) groups in the fluorescent BODIPY dyes was shown to improve the emission intensity observed for the anti-body conjugates with high degrees of labelling (DOL>4).

Thus, the phosphorylated BODIPY dyes represent a new valuable addition to the family of the bright, photostable, water-soluble fluorescent markers for the use in optical microscopy.

Spectral Properties of the New Dyes and their Use in Microscopy

The Stokes shifts of the green-emitting coumarin dyes 10, 11, 18, 20 were found to be ca. 70-80 nm. For example, the Stokes shift of the phosphorylated hydrophilic coumarin dye 11 is 79 nm; its absorption band matches the excitation line of the violet 405 nm laser. Therefore, dye 11 can be efficiently used in microscopy together with numerous fluorescent labels (e. g. Alexa™ Fluor 488, Oregon Green™ 488) which also emit green light, but absorb strongly at about 480-490 nm. The latter dyes possess small Stokes shifts; they emit light upon excitation with 488 nm line of Argon laser. The fluorescence quantum yields of the dyes 10, 11, 18, 20 were found to be high. In order to compare the spectral properties of the phosphorylated coumarin dyes with those of sulfonylated ones, we prepared the hydrophilic coumarin dye 20 with a sulfonic acid residue attached to the same position, at which compound 11 bears the phosphorylated hydroxy group (Scheme 5). The emission and absorption spectra of compound 11 and its analogue 20 are very similar (Table 1). However, after attaching to antibodies, the fluorescence quantum yields of the conjugates obtained from the phosphorylated coumarin dye 11 was found to be significantly higher (30%) than that of the conjugates prepared from the sulfonated dye 20 (18%).

TABLE 1

Spectral data of inventive coumarin and rhodamine dyes and their bioconjugates.*

| Compd. | $\lambda_{max}$ (abs.) nm | $\lambda_{max}$ (fl.) nm | Solvent (pH) | $\epsilon \cdot 10^{-4} M^{-1} cm^{-1}$ | DOL | $\Phi_{fl}\%$ | $\tau_1$ ns (amp) | $\tau_2$ ns (amp) | Remarks |
|---|---|---|---|---|---|---|---|---|---|
| 10 | 430 | 501 | MeOH | 3.07 | | 82 | | | Low solubility in water |
| 11 | 436 | 515 | PBS (7.4) | 2.27 | | 68 | 3.3 | — | |
| 11-AB | 439 | 513 | PBS (7.4) | — | 2.6 | 30 | 3.2 (12) | 0.29 (0.32) | Sheep anti-mouse AB |
| 13 | 516 | 614 | MeOH | 5.57 | | 10 | | | Low solubility in water |
| 18 | 437 | 507 | MeOH | 3.34 | | 77 | | | Low solubility in water |
| 20-H | 436 | 510 | MeOH | 2.59 | | 56 | | | |
| 20-H | 436 | 515 | PBS (7.4) | 3.12 | | 57 | | | |
| 20-AB | 437 | 512 | PBS (7.4) | — | 2.7 | 18 | | | Sheep anti-mouse AB |
| 24-H | 632 | 654 | $H_2O$ | 8.6 | | 85 | | | Limited solubility in water |
| 24-H-AB | 637 | 657 | PBS (7.4) | — | 0.7 | 66 | | | Goat anti-rabbit AB |
| 26-H | 635 | 655 | $H_2O$ | 7.5 | | 83 | 3.0 | — | |
| 26-H-AB | 640 | 660 | PBS (7.4) | — | 2.5 | 51 | | | Sheep anti-mouse AB |

*$\lambda_{max}$ (abs.), $\lambda_{max}$ (fl.): absorption and fluorescence maxima, respectively; PBS: phosphate buffer saline; $\epsilon$: molar extinction coefficient; DOL: degree of labeling; $\Phi_{fl}$: fluorescence quantum yield; $\tau_{1,2}$: lifetime of the excited state (biexponential fit, monoexponential fit if $\tau_2$ is absent); amp: amplitudes (integral) for the corresponding component in biexponential fits; AB—antibodies

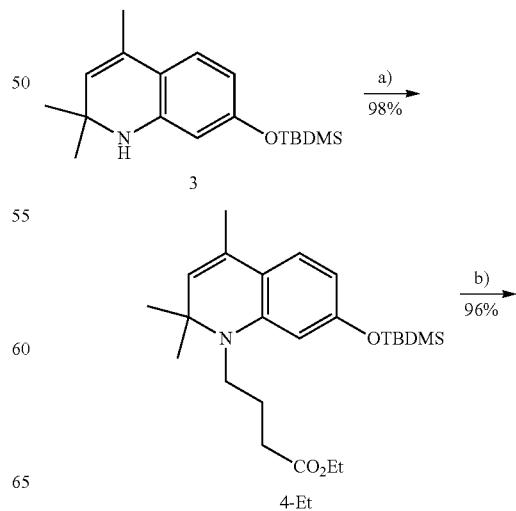

Scheme 5. Preparation of the reference fluorescent dye 20.

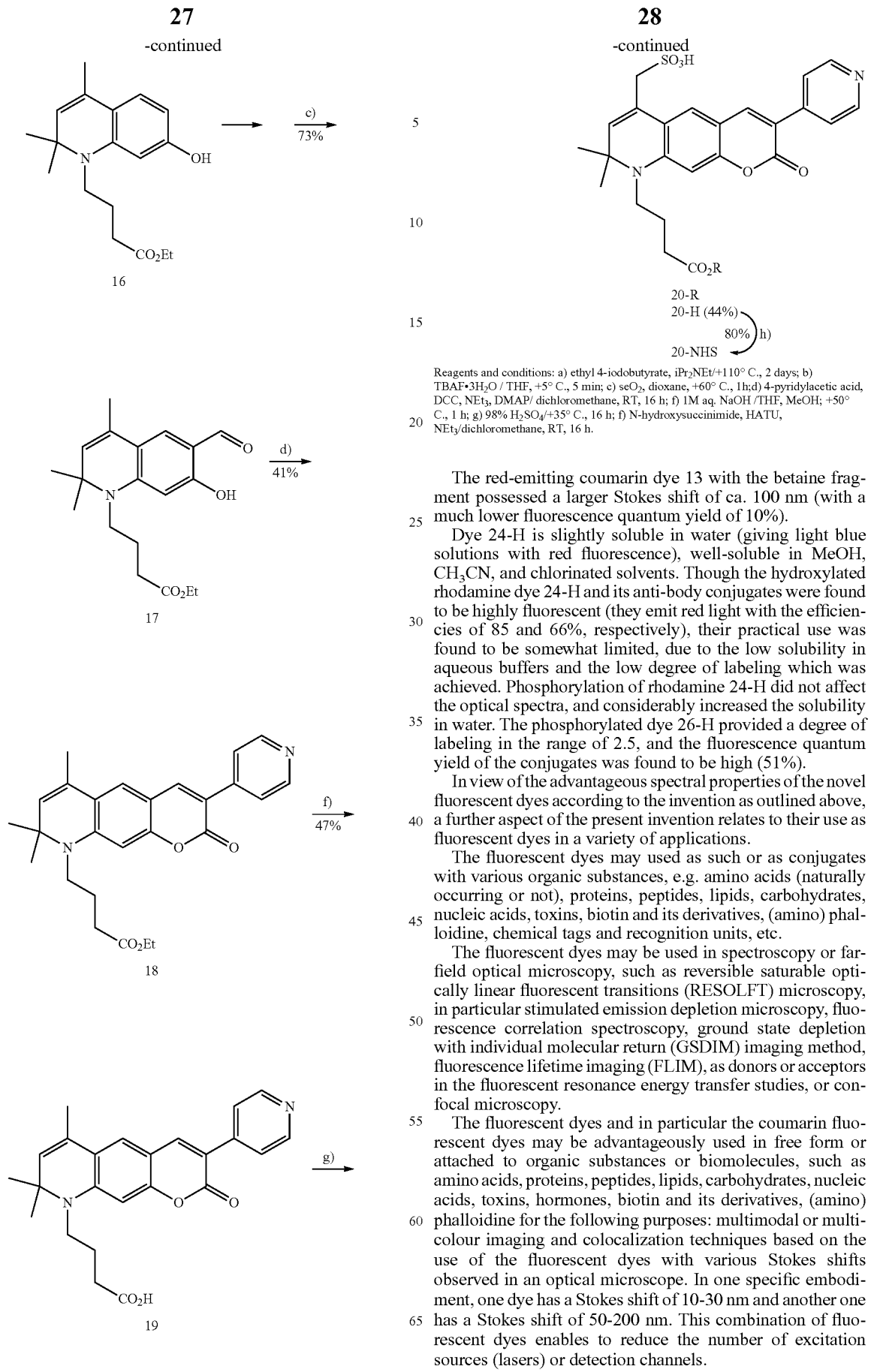

Reagents and conditions: a) ethyl 4-iodobutyrate, iPr₂NEt/+110° C., 2 days; b) TBAF·3H₂O / THF, +5° C., 5 min; c) seO₂, dioxane, +60° C., 1h;d) 4-pyridylacetic acid, DCC, NEt₃, DMAP/ dichloromethane, RT, 16 h; f) 1M aq. NaOH /THF, MeOH; +50° C., 1 h; g) 98% H₂SO₄/+35° C., 16 h; f) N-hydroxysuccinimide, HATU, NEt₃/dichloromethane, RT, 16 h.

The red-emitting coumarin dye 13 with the betaine fragment possessed a larger Stokes shift of ca. 100 nm (with a much lower fluorescence quantum yield of 10%).

Dye 24-H is slightly soluble in water (giving light blue solutions with red fluorescence), well-soluble in MeOH, CH₃CN, and chlorinated solvents. Though the hydroxylated rhodamine dye 24-H and its anti-body conjugates were found to be highly fluorescent (they emit red light with the efficiencies of 85 and 66%, respectively), their practical use was found to be somewhat limited, due to the low solubility in aqueous buffers and the low degree of labeling which was achieved. Phosphorylation of rhodamine 24-H did not affect the optical spectra, and considerably increased the solubility in water. The phosphorylated dye 26-H provided a degree of labeling in the range of 2.5, and the fluorescence quantum yield of the conjugates was found to be high (51%).

In view of the advantageous spectral properties of the novel fluorescent dyes according to the invention as outlined above, a further aspect of the present invention relates to their use as fluorescent dyes in a variety of applications.

The fluorescent dyes may used as such or as conjugates with various organic substances, e.g. amino acids (naturally occurring or not), proteins, peptides, lipids, carbohydrates, nucleic acids, toxins, biotin and its derivatives, (amino) phalloidine, chemical tags and recognition units, etc.

The fluorescent dyes may be used in spectroscopy or far-field optical microscopy, such as reversible saturable optically linear fluorescent transitions (RESOLFT) microscopy, in particular stimulated emission depletion microscopy, fluorescence correlation spectroscopy, ground state depletion with individual molecular return (GSDIM) imaging method, fluorescence lifetime imaging (FLIM), as donors or acceptors in the fluorescent resonance energy transfer studies, or confocal microscopy.

The fluorescent dyes and in particular the coumarin fluorescent dyes may be advantageously used in free form or attached to organic substances or biomolecules, such as amino acids, proteins, peptides, lipids, carbohydrates, nucleic acids, toxins, hormones, biotin and its derivatives, (amino) phalloidine for the following purposes: multimodal or multi-colour imaging and colocalization techniques based on the use of the fluorescent dyes with various Stokes shifts observed in an optical microscope. In one specific embodiment, one dye has a Stokes shift of 10-30 nm and another one has a Stokes shift of 50-200 nm. This combination of fluorescent dyes enables to reduce the number of excitation sources (lasers) or detection channels.

BRIEF DESCRIPTION OF THE FIGURES

The patent or application file contains at least one drawing executed in color. Copies of this patent or patent application publication with color drawing(s) will be provided by the Office upon request and payment of the necessary fee.

Figure 1:
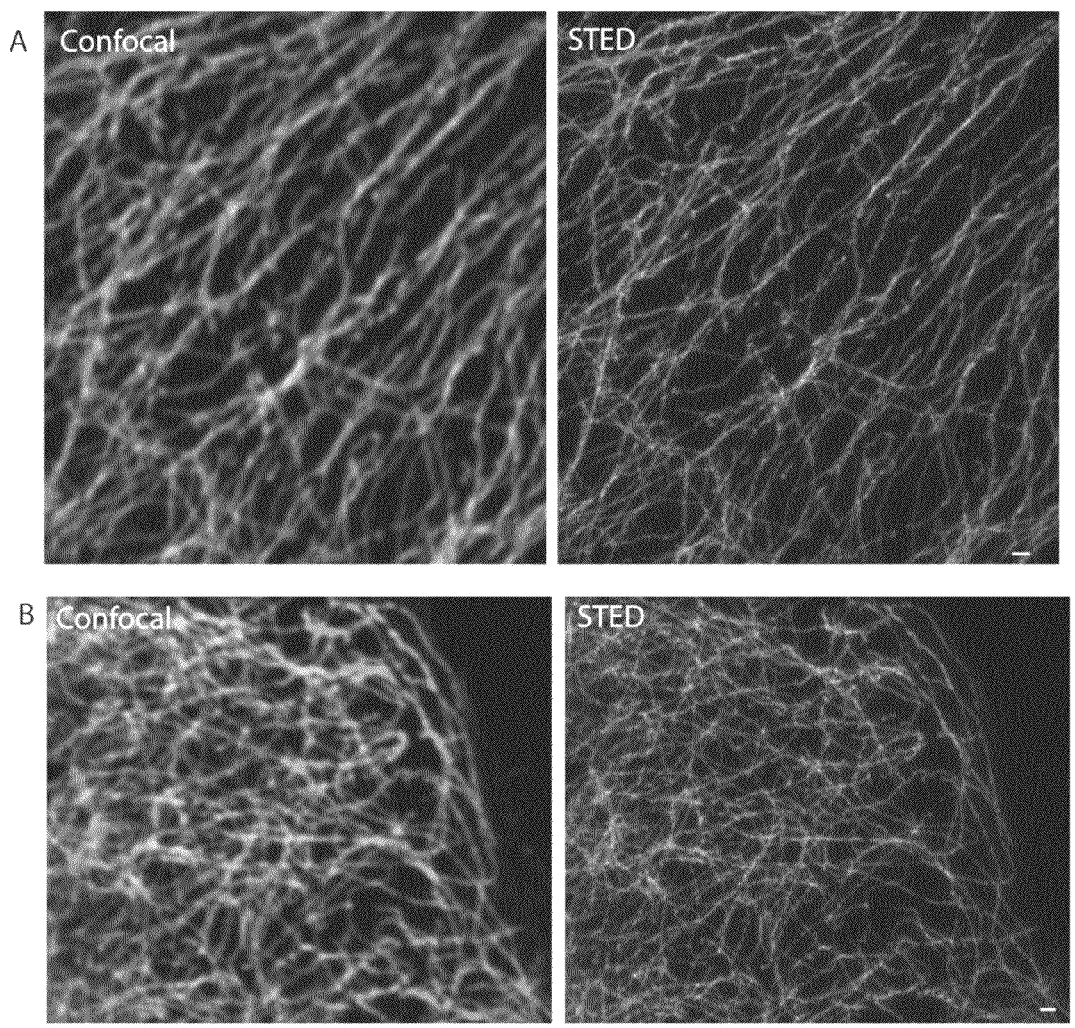
FIG. 1 shows confocal and STED microscopy images of vimentin (red) and tubulin (green) filaments in a fixed mammalian PtK2 (*Potorous tridactylus*, kidney) cell. The vimentin skeleton was immunolabeled with NHS ester 12 (dye 11, Table 1); the tubulin skeleton was immunolabeled with Oregon Green™ 488

The following Examples illustrate the present invention in more detail.

General Materials and Methods

UV-visible absorption spectra were recorded on a Varian Cary 4000 UV-Vis spectrophotometer, and fluorescence spectra on a Varian Cary Eclipse fluorescence spectrophotometer. Reactions were carried out with magnetic stirring in Schlenk flasks equipped with septa or reflux condensers with bubble-counters under argon using a standard manifold with vacuum and argon lines. The MICROTOF spectrometer equipped with ESI ion source Apollo and direct injector with LC autosampler Agilent RR 1200 was used for obtaining mass spectra and high resolution mass-spectra (ESI-HRMS). ESI-HRMS were obtained also on APEX IV spectrometer (Bruker). ESI spectra were also obtained on a Varian 500MS spectrometer in some cases. HPLC system (Knauer): Smartline pump 1000 (2×), UV detector 2500, column thermostat 4000 (25° C.), mixing chamber, injection valve with 20 and 100 μL loop for analytical and preparative columns, respectively; 6-port-3-channel switching valve; analytical column: Eurospher-100 C18, 5 μm, 250×4 mm, 1.2 mL/min; preparative column: Eurospher-100-5 C18, 5 μm, 250×8 mm, 4 mL/min; solvent A: water+0.1% v/v trifluoroacetic acid (TFA); solvent B: $CH_3CN$+0.1% v/v TFA; detection at 636 nm (if not stated otherwise). Normal phase analytical TLC was performed on MERCK ready-to-use plates with silica gel 60 ($F_{254}$).

EXAMPLE 1

Synthesis of Phosphorylated Fluorescent Dyes and their Precursors

Synthesis of Precursors to Coumarin Dyes According to Scheme 1:

3-[(tert-Butyldimethylsilyl)oxy]aniline (2). 3-Aminophenol (21.8 g, 0.200 mol) and imidazole (34 g, 0.50 mol) were dissolved in DMF (200 mL), the solution was cooled with an ice-water bath, and TBDMSCl (36.1 g, 0.24 mol) was added in one portion. The cooling bath was removed, the reaction mixture was allowed to warm-up to room temperature, and stirred for 1 h. DMF (ca. 150 mL) was evaporated in vacuo at +55° C., the residue was diluted with AcOEt (250 mL), washed with sat. aq. $NaHCO_3$ (twice), water (several times), brine and dried over $MgSO_4$. After evaporation of solvents, the oily residue was dried in vacuo (0.5 Torr) to a constant weight. Purification by column chromatography (gradient elution with hexane to hexane/ether=5/1) afforded compound 2 ($R_f$=0.24 in hexane/ether=8/1) as a clear oil (34.1 g, 76%). $^1$H NMR (300 MHz, $CDCl_3$): δ=0.21 (s, 6 H, Si$\underline{Me}_2Bu^t$), 0.99 (s, 9 H, $SiMe_2\underline{Bu}^t$), 3.60 (br. s, 2 H, $NH_2$), 6.18 (m, 1 H), 6.28 (m, 2 H), 6.98 (m, 1 H) ppm.

7-[(tert-Butyldimethylsilyl)oxy]-1,2-dihydro-2,2,4-trimethylquinoline (3). Anhydrous ytterbium(III) triflate (ALDRICH; 4.2 g, 6.8 mmol, freshly dried in vacuo at +130° C. for 4 h) was added in one portion to a solution of compound 2 (23.3 g, 0.105 mol) in dry acetone (300 mL). The reaction mixture was stirred at RT for 16 h. Acetone was evaporated in vacuo, the residue was dissolved in AcOEt, washed with sat. aq. $NaHCO_3$ (twice), water, brine and dried over $MgSO_4$. After evaporation of solvents, the oily residue was dried in vacuo (0.5 Torr) to a constant weight. Purification by column chromatography (gradient elution with hexane to hexane/ether=10/1) afforded compound 3 ($R_f$=0.86, hexane/ether=8/1) as a clear oil (19.85 g, 63%). $^1$H NMR (300 MHz, $CDCl_3$): δ=0.20 (s, 6 H, Si$\underline{Me}_2Bu^t$), 0.98 (s, 9 H, $SiMe_2\underline{Bu}^t$), 1.27 (s, 6 H, 2×Me), 1.96 (d, J=0.8 Hz, 3 H, Me), 5.19 (d, J=0.8 Hz, 1 H, $\underline{H}C=$), 5.98 (dd, J=1.8 and 0.4 Hz, 1 H), 6.14 (dd, J=8.5 and 1.8 Hz, 1 H), 6.91 (dd, J=8.5 and 0.4 Hz, 1 H) ppm.

1-[3-(tert-Butoxycarbonyl)propyl]-7-[(tert-butyldimethylsilyl)-oxy]-1,2-dihydro-2,2,4-trimethylquinoline (4).

N-Isopropyl-N,N-diethylamine (8.17 g, 63.4 mmol) was added to a mixture of compound 3 (9.60 g, 31.7 mmol) and t-butyl 3-iodobutyrate [a] V. Chaleix, V. Sol, Y.-M. Huang, M. Guilloton, R. Granet, J. C. Blais, P. Krausz, *Eur. J. Org. Chem.* 2003, 1486-1493; b) M. P. Glenn, P. Kahnberg, G. M. Boyle, K. A. Hansford, D. Hans, A. C. Martyn, P. G. Parsons, D. P. Fairlie *J. Med. Chem.* 2004, 47, 2984-2994] (10.7 g, 34.9 mmol) in a screw-cup bottle, and the reaction mixture was stirred at +110° C. (bath temp.) for 4 days. After cooling, the reaction mixture was diluted with diethyl ether, passed through a plug of silica gel (eluting with ether), and the solvents were evaporated in vacuo. The residue was dissolved in a hexane/ether (3/1) mixture, washed with sat. aq. $NaHCO_3$, and the solution was passed again through a plug of silica gel (eluting with hexane/ether (3/1) mixture). According to TLC (hexane/ether=10/1), two spots were detected in the eluate: that of compound 3 ($R_f$=0.48) and compound 4 ($R_f$=0.43). After evaporation of solvents in vacuo, the oily residue was distilled in the Kugelrohr distillation apparatus. Compound 4 (4.16 g, 27% yield) was collected at 180° C. (0.6 Torr). The first fraction (4.0 g, b.p. 150° C. at 0.6 Torr) was shown to be compound 3 (ca. 95% pure), and the second one (2.0 g, b.p. 150-180° C. at 0.6 Torr) a mixture of compounds 3 and 4 in ca. 1/3 ratio. $^1$H NMR (300 MHz, $CDCl_3$): δ=0.21 (s, 6 H, Si$\underline{Me}_2Bu^t$), 0.98 (s, 9 H, $SiMe_2\underline{Bu}^t$), 1.28 (s, 6 H, 2×Me), 1.46 (s, 9 H, $CO_2\underline{Bu}^t$), 1.86 (m, 2 H, $NCH_2C\underline{H}_2CH_2CO_2Bu^t$), 1.95 (d, J=0.5 Hz, 3 H, Me), 2.30 (m, 2 H, $NCH_2CH_2C\underline{H}_2CO_2Bu^t$), 3.20 (m, 2 H, $NC\underline{H}_2CH_2CH_2CO_2Bu^t$), 5.10 (d, J=0.5 Hz, 1 H, $\underline{H}C=$), 6.02 (dd, J=1.8 and 0.4 Hz, 1 H), 6.10 (dd, J=8.5 and 1.8 Hz, 1 H), 6.88 (dd, J=8.5 and 0.4 Hz, 1 H) ppm.

1-[3-(tert-Butoxycarbonyl)propyl]-7-[(tert-butyldimethylsilyl)-oxy]-1,2-dihydro-4-formyl-2,2-dimethylquinoline (5) and 1-[3-(tert-Butoxycarbonyl)propyl]-7-[(tert-butyldimethyl-silyl)oxy]-1,2-dihydro-4-hydroxymethyl-2,2-dimethylquinoline (6a).

SeO$_2$ (1.50 g, 13.5 mmol) was added in portions to a hot (60° C.) solution of compound 4 (3.24 g, 6.74 mmol) in dioxane (50 mL). Then the reaction mixture was at this temperature for 1 h. After cooling, it was diluted with ether, and the organic layer was washed with sat. aq. NaHCO$_3$ and dried over MgSO$_4$. Solvents were evaporated, and the residue was purified by column chromatography (with hexane/ether/dichloromethane [10/3/1] as an eluent). After evaporation of solvents, the compound 5 (1.3 g) was dissolved in THF/MeOH (20/1), and NaBH$_4$ (100 mg, 2.6 mmol) was added in portions at room temp. After 5 min, the reaction was complete (TLC). The excess of NaBH$_4$ was destroyed by adding acetone (0.5 mL); all volatile materials were evaporated in vacuo, and the alcohol 6a was isolated by column chromatography (with hexane/ether/dichloromethane/MeOH mixture (10/3/4/0.3) as an eluent; R$_f$=0.42); yield 0.745 g (22%) of light yellow oil.

Compound 5. $^1$H NMR (300 MHz, CDCl$_3$): δ=0.21 (s, 6 H, SiMe$_2$Bu$^t$), 0.98 (s, 9 H, SiMe$_2$Bu$^t$), 1.40 (s, 6 H, 2×Me), 1.45 (s, 9 H, CO$_2$Bu$^t$), 1.86 (m, 2 H, NCH$_2$CH$_2$CH$_2$CO$_2$Et), 2.30 (m, 2 H, NCH$_2$CH$_2$CH$_2$CO$_2$Et), 3.22 (m, 2 H, NCH$_2$CH$_2$CH$_2$CO$_2$Et), 6.04 (s, 1 H, HC=), 6.20 (m, 2 H), 8.08 (m, 1 H), 9.58 (s, 1 H, CHO) ppm.

Compound 6a. $^1$H NMR (300 MHz, CDCl$_3$): δ=0.21 (s, 6 H, SiMe$_2$Bu$^t$), 0.98 (s, 9 H, SiMe$_2$Bu$^t$), 1.30 (s, 6 H, 2×Me), 1.44 (s, 9 H, CO$_2$Bu$^t$), 1.86 (m, 2 H, NCH$_2$CH$_2$CH$_2$CO$_2$Bu$^t$), 2.30 (m, 2 H, NCH$_2$CH$_2$CH$_2$CO$_2$Bu$^t$), 3.20 (m, 2 H, NCH$_2$CH$_2$CH$_2$CO$_2$Bu$^t$), 4.42 (br. s, 2 H, CH$_2$OH), 5.35 (s, 1 H, HC=), 6.08 (m, 2 H), 6.97 (m, 1 H) ppm.

Compound 7a. A solution of di-tert-butyl N,N-diisopropylphosphoramidite (744 mg, 3.04 mmol) in THF (3 mL) was added to a solution of compound 5 (700 mg, 1.52 mmol) in THF (12 mL) followed by 1H-tetrazole (0.45 M in acetonitrile, 6.75 mL, 3.04 mmol). The reaction mixture was stirred at 40° C. for 1 h, cooled in an ice-water bath, and a solution of 70% m-chloroperoxybenzoic acid (748 mg, 3.04 mmol) in dichloromethane (5 mL) was added in one portion. After 15 min, the reaction was quenched by adding 10% aq. Na$_2$SO$_3$ (10 mL). Diethyl ether (50 mL) was added, and the organic layer was separated and washed with sat. NaHCO$_3$, water, brine and dried over MgSO$_4$. After evaporation of solvents, the oily residue was purified by column chromatography (gradient elution with hexane/ether, 2/1→1/1). The product 7a (R$_f$=0.32 in hexane/ether, 1/2) was obtained as viscous oil; yield 410 mg (41%). $^1$H NMR (300 MHz, CDCl$_3$): δ=0.21 (s, 6 H, SiMe$_2$Bu$^t$), 0.98 (s, 9 H, SiMe$_2$Bu$^t$), 1.34 (s, 6 H, 2×Me), 1.43 (s, 9 H, CO$_2$Bu$^t$), 1.47 (s, 18 H, OPO(OBu$^t$)$_2$), 1.84 (m, 2 H, NCH$_2$CH$_2$CH$_2$CO$_2$Bu$_t$), 2.26 (m, 2 H, NCH$_2$CH$_2$CH$_2$CO$_2$Bu$^t$), 3.20 (m, 2 H, NCH$_2$CH$_2$CH$_2$CO$_2$Bu$_t$), 4.72 (m, 2 H, CH$_2$OPO(OBu$^t$)$_2$), 5.40 (m, 1 H, HC=), 6.05 (m, 2 H), 6.94 (m, 1 H) ppm.

Compound 8a. A solution of TBAF.3H$_2$O (173 mg, 0.551 mmol) in THF (0.5 mL) was added to a solution of compound 7a (360 mg, 0.551 mmol) in THF at +5° C. After 5 min, the reaction mixture was diluted with ether (10 mL), washed with water (2×) and dried over MgSO$_4$. After evaporation of solvents, the residue was purified by column chromatography (gradient elution with ether/hexane mixture, 2/1 to 4/1). Phenol 8a (R$_f$=0.24 in hexane/ether, 1/4) was isolated in 84% yield (249 mg). $^1$H NMR (300 MHz, CDCl$_3$): δ=1.27 (s, 6 H, 2×Me), 1.43 (s, 9 H, CO$_2$Bu$^t$), 1.47 (s, 18 H, OPO(OBu$^t$)$_2$), 1.82 (m, 2 H, NCH$_2$CH$_2$CH$_2$CO$_2$Bu$^t$), 2.24 (m, 2 H, NCH$_2$CH$_2$CH$_2$CO$_2$Bu$^t$), 3.18 (m, 2 H, NCH$_2$CH$_2$CH$_2$CO$_2$Bu$^t$), 4.68 (d, J$_{H-P}$=7.2 Hz, 2 H, CH$_2$OP), 5.32 (s, 1 H, HC=), 6.07 (d, J=1.8 Hz, 1 H), 6.23 (dd, J=8.4 and 1.8 Hz, 1 H), 6.92 (d, J=8.4 Hz, 1 H) ppm. $^{13}$C NMR (75.5 MHz, CDCl$_3$): δ=24.0, 28.4, 28.5, 30.3 (J$_{C,P}$=4.5 Hz), 33.4 43.8, 57.1, 67.3 (J$_{C,P}$=5.3 Hz), 80.8, 83.3 J$_{C,P}$=7.5 Hz), 99.2, 103.4, 113.0, 124.9, 127.9 (J$_{C,P}$=7.5), 128.3, 145.8, 158.6, 173.2 ppm. MS (ESI): m/z (negative mode, rel. int., %)=1077.5 [2M–H]$^-$, 538.3 [M–H]–; HRMS (C$_{28}$H$_{45}$NO$_7$P): 538.2936 (found [M–H]$^-$), 538.2939 (calc.); m/z (positive mode, rel. int., %) 1101.6 (100) [2M+Na]$^+$, 562.3 (93) [M+Na]$^+$, 540.3 (11) [M+H]$^+$; HRMS (C$_{28}$H$_{47}$NO$_7$P): 540.3075 (found [M+H]$^+$), 540.3085 (calc.).

Compound 9a. POCl$_3$ (62 mg, 0.40 mmol) was added to DMF (2 mL) at +5° C., and the mixture was allowed to warm to room temperature. After stirring for 15 min at room temperature, it was cooled down (+5° C.), and a solution of phenol 8a (145 mg, 0.269 mmol) in DMF (1 mL) was added slowly. The cooling bath was removed, and the reaction mixture was allowed to warm up to room temperature, stirred for 4 h, and finally heated at 50° C. for 15 min. The TLC control of this reaction is difficult, because the product was found to have the same R$_f$ value, as the starting material (in most solvents). After cooling, the reaction was "quenched" by adding 1 mL of sat. aq. NaHCO$_3$, and the product 9a was extracted with dichloromethane. The organic layer was dried (MgSO$_4$), and, after evaporation of solvents, the residue was purified by column chromatography (gradient elution with hexane/ether mixture, 1/1 to 1/4). Yield 127 mg (83%). $^1$H NMR (300 MHz, CDCl$_3$): δ=1.38 (s, 6 H, 2×Me), 1.44 (s, 9 H, CO$_2$Bu$^t$), 1.45 (s, 18 H, OPO(OBu$^t$)$_2$), 1.86 (m, 2 H, NCH$_2$CH$_2$CH$_2$CO$_2$Bu$^t$), 2.30 (m, 2 H, NCH$_2$CH$_2$CH$_2$CO$_2$Bu$^t$), 3.30 (m, 2 H, NCH$_2$CH$_2$CH$_2$CO$_2$Bu$^t$), 4.70 (d, J$_{H-P}$=7.2 Hz, 2 H, CH$_2$OP), 5.46 (s, 1 H, HC=), 5.95 (s, 1 H, Ar), 7.16 (s, 1 H, Ar), 9.44 (s, 1 H, CHO), 11.72 (s, 1 H, OH) ppm. $^{13}$C NMR (75.5 MHz, CDCl$_3$): δ=23.0, 28.1, 29.0, 29.9 (J$_{C,P}$=4.5),32.7, 44.1, 58.2, 66.1, (J$_{C,P}$=5.3), 80.8, 82.6 (J$_{C,P}$=7.5)96.8, 111.0, 112.7, 126.15 (J$_{C,P}$=8.2)128.4, 129.2, 151.0, 164.7, 172.0, 192.1 ppm. MS (ESI): m/z (negative mode, rel. int., %)=566.3 (100), [M–H]$^-$; HRMS (C$_{29}$H$_{45}$NO$_8$P): 566.2885 (found [M–H]$^-$), 566.2888 (calc.); m/z (positive mode, rel. int., %)=1157.6 (98) [2M+Na]$^+$, 590.3 (100) [M+Na]$^+$; HRMS (C$_{29}$H$_{46}$NO$_8$PNa): 590.2857 (found [M+Na]$^+$), 590.2853 (calc.).

Synthesis of Coumarin Dyes According to Scheme 2:

Coumarin 10. 4-Pyridylacetic acid hydrochloride (58 mg, 0.34 mmol) was added with stirring to a solution of compound 9a (127 mg, 0.224 mmol) in dichloromethane (10 mL). Then Et$_3$N (59 mg, 0.58 mmol) was added, and, after 10 min, N,N'-dicyclohexylcarbodiimide (92 mg, 0.45 mmol) and 4-dimethylaminopyridine (3.0 mg, 0.022 mmol) were added. The reaction mixture was stirred for 16 h, filtered through a plug of silica gel (using dichloromethane/ether mixture (2/1) as eluent). After evaporation of solvents, the product 10 was isolated by column chromatography (eluting with dichloromethane to dichloromethane/ether mixture, 2/1). After evaporation of solvents, compound 10 was precipitated from ether with hexane. Yield: 35 mg (23%) of light-yellow crystals. MS (ESI): m/z (positive mode, rel. int., %)=669.4 (100) [M+H]$^+$. λ$_{abs}$=430 nm, λ$_{em}$=501 nm, ε=30700 M$^{-1}$cm$^{-1}$, Φ$_{fl.}$=0.82 (MeOH).

Coumarin Dye 11. Compound 10 (12 mg, 0.018 mmol) was dissolved in TFA (0.5 mL). After 4 h, TFA was evaporated and the free acid 11 was precipitated from ether giving 7.8 mg (87% yield) of dye 11 as a brown solid. MS (ESI): m/z (negative mode, rel. int., %)=521.2 (30) [M+Na-2H]$^-$, 499 (57) [M–H]–. HPLC: t$_R$=9.2 min (MeCN/H$_2$O (+0.1% v/v TFA in H$_2$O and MeCN): 20/80-50/50 in 25 min, column 4×250 mm, 1.2 mL/min, detection at 433 nm); $\lambda_{abs}$=436 nm, $\lambda_{em}$=515 nm, $\epsilon$=22700 M$^{-1}$cm$^{-1}$, $\Phi_{fl.}$=0.68 (in PBS buffer at pH 7.4).

NHS Ester 12. Acid 11 (5.0 mg, 10 µmol) was dissolved in DMF (0.5 mL), N-hydroxysuccinimide (1.7 mg, 15 µmol) was added at room temperature followed by HATU (4 mg, 15 µmol) and NEt$_3$ (3.0 mg, 30 µmol). The reaction mixture was stirred at room temperature for 16 h. After that, the reaction mixture was subjected to chromatography (without additional work-up). Gradient elution with acetone-acetone/acetonitrile/water (4/4/1) afforded NHS ester 12. MS (ESI in MeOH): m/z (negative mode, rel. in %)=628.2 (100) [M+CH$_3$OH—H]$^-$, 596.2 (55) [M—H]$^-$; HRMS (C$_{29}$H$_{27}$N$_3$O$_{10}$P): 596.1438 (found for [M−H]$^-$), 596.1440 (calc.). HPLC: $t_R$=12.4 min (MeCN/H$_2$O (+0.1% v/v TFA in H$_2$O and MeCN)=20/80-50/50 in 25 min, column 4×250 mm, 1.2 mL/min, detection at 433 nm). The conjugate with anti sheep anti-mouse IG had the following properties in PBS buffer at pH 7.4: $\lambda_{abs}$=439 nm, $\lambda_{em}$=513 nm, $\Phi_{fl.}$=0.30, degree of labeling (DOL)=2.6.

Compound 13. Perfluorocyclopentene (0.2 mL) was added to a cold (ice-water bath) solution of compound 10 (12 mg, 0.018 mmol) in aqueous EtOH (95% v/v) in a screw-cup bottle. The reaction vessel was closed, and the mixture was heated at 60° C. for 3 h. After cooling, all volatile materials were evaporated in vacuo, and the residue was purified by column chromatography (AcOEt→AcOEt/acetone/dichloromethane, 6/3/1; $R_f$=0.84 in AcOEt/acetone/dichloromethane=6/3/1.5). The red-colored fractions were collected, and, after evaporation of solvents the residue was triturated with ether/hexane mixture affording 7.2 mg (48%) of compound 13. MS (ESI): m/z (negative mode, rel. int. %)=871.1 (10) [M+Cl]$^-$; m/z (positive mode, %)=859.3 (83) [M+Na]$^+$. $\lambda_{abs}$=516 nm, $\lambda_{em}$=614 nm, $\epsilon$=55700 M$^{-1}$ cm$^{-1}$, $\Phi_{fl.}$=0.10 (in MeOH).

Carboxylic and Phosphoric Acid 14. Ester 13 (6 mg, 7.2 µmol) was dissolved in TFA (0.5 mL). After keeping at room temperature for 16 h, TFA was evaporated, and acid 14 was precipitated from ether affording 4.5 mg (93%) of a red solid. MS (ESI): m/z (negative mode, rel. int., %)=667.1 [M−H]$^-$; m/z (positive mode, rel. int. %)=735.5 (42) [M+3Na−2H]$^+$; HPLC: $t_R$=21.2 min (MeCN/H$_2$O (+0.1% v/v TFA in H$_2$O and MeCN)=20/80-50/50 in 25 min, column 4×250 mm, 1.2 mL/min, detection at 552 nm).

NHS Ester 15. The acid 14 (3.4 mg, 5 µmol) was dissolved in DMF (1 mL), N-hydroxysuccinimide (0.9 mg, 7.5 µmol) was added at room temperature followed by HATU (2 mg, 7.5 µmol) and NEt$_3$ (1.5 mg, 15 µmol). The reaction mixture was stirred at room temperature for 16 h. Then it was subjected to chromatography without additional work-up (with acetone→acetone/acetonitrile/water (10/10/1)).

Synthesis of the Reference Coumarin Dyes 18-20 According to Scheme 6:

Ethyl Ester 4-Et. DIEA (11.8 g, 91.7 mmol) was added to a mixture of compound 3 (13.9 g, 45.87 mmol) and ethyl 3-iodobutyrate (13.3 g, 55.05 mmol) in a screw-cup bottle, and the reaction mixture was stirred with heating (110° C.) for 2 days. After cooling, the reaction mixture was diluted with diethyl ether, passed through a plug of silica gel (eluting with ether), and the filtrate evaporated in vacuo. The residue was dissolved in hexane/ether (3/1) mixture, washed with water, brine and dried over MgSO$_4$. The product 4-Et was isolated by a short path column chromatography (hexane→hexane/ether 10/1; $R_f$=0.59 in hexane/ether=10/1); yield 18.75 g (98.5%) of a clear oil. $^1$H NMR (300 MHz, CDCl$_3$): δ=0.21 (s, 6 H, SiMe$_2$Bu$^t$), 0.98 (s, 9 H, SiMe$_2$Bu$^t$), 1.26 (t, J=7.2 Hz, 3 H, CO$_2$CH$_2$CH$_3$), 1.28 (s, 6 H, 2×Me), 1.90 (m, 2 H, NCH$_2$CH$_2$CH$_2$CO$_2$Et), 1.93 (d, J=0.5 Hz, 3H, Me), 2.38 (m, 2 H, NCH$_2$CH$_2$CH$_2$CO$_2$Et), 3.20 (m, 2 H, NCH$_2$CH$_2$CH$_2$CO$_2$Et), 4.16 (q, J=7.2 Hz, 2 H, CO$_2$CH$_2$CH$_3$), 5.10 (d, J=0.5 Hz, 1 H, HC=), 6.02 (m, 1 H), 6.10 (m, 1 H) 6.90 (m, 1 H) ppm.

Phenol 16. A solution of 1 M TBAF in THF (30 mL, 30 mmol) was added to a solution of ester 4-Et (12.48 g, 29.93 mmol) in THF (50 mL) at +5° C. After 5 min, the reaction mixture was diluted with ether (150 mL), washed with water (2×) and brine. The combined aqueous layers were extracted with ether, and the combined organic solutions were dried (MgSO$_4$). After evaporation of solvents, the residue was purified by column chromatography (ether/hexane, 2/1→4/1). Phenol 16 ($R_f$=0.07 in hexane/ether, 1/5) was isolated in 99% yield (8.98 g). $^1$H NMR (300 MHz, CDCl$_3$): δ=1.27 (s, 6 H, 2×Me), 1.27 (t, J=7.2 Hz, 3 H, CO$_2$CH$_2$CH$_3$), 1.95 (m, 2 H, NCH$_2$CH$_2$CH$_2$CO$_2$Et), 1.95 (d, J=0.5 Hz, 3 H, Me), 2.40 (m, 2 H, NCH$_2$CH$_2$CH$_2$CO$_2$Et), 3.20 (m, 2 H, NCH$_2$CH$_2$CH$_2$CO$_2$Et), 4.18 (q, J=7.2 Hz, 2 H, CO$_2$CH$_2$CH$_3$), 5.08 (d, J=0.5 Hz, 1 H, HC=), 6.10 (m, 2 H), 6.90 (m, 1 H) ppm.

Aldehyde 17. POCl$_3$ (3.90 g, 25.5 mmol) was added to DMF (30 mL) at +5° C., and the mixture was allowed to warm to room temp. After stirring for 15 min, it was cooled again to +5° C., and a solution of phenol 16 (5.15 g, 17.0 mmol) in DMF (15 mL) was added slowly. The cooling bath was removed, the reaction mixture was allowed to warm up to room temp., and finally heated at +50° C. for 30 min. (The starting material had $R_f$=0.40, and the product $R_f$=0.54 in hexane/AcOEt=10/3). After cooling, the reaction was "quenched" by adding of 15 mL of sat. aq. NaHCO$_3$, and the product 17 was extracted with dichloromethane. The organic solutions were dried (MgSO$_4$), and, after evaporation of the solvent, subjected to column chromatography (cyclohexane/AcOEt, 2/1) yielding 3.59 g (64%) of the title compound as a viscous oil. $^1$H NMR (300 MHz, CDCl$_3$): δ=1.30 (t, J=7.2 Hz, 3 H, CO$_2$CH$_2$CH$_3$), 1.39 (s, 6 H, 2×Me), 1.95 (m, 2 H, NCH$_2$CH$_2$CH$_2$CO$_2$Et), 195 (d, J=0.5 Hz, 3 H, Me), 2.40 (m, 2 H, NCH$_2$CH$_2$CH$_2$CO$_2$Et), 3.34 (m, 2 H, NCH$_2$CH$_2$CH$_2$CO$_2$Et), 4.18 (q, J=7.2 Hz, 2 H, CO$_2$CH$_2$CH$_3$), 5.09 (d, J=0.5 Hz, 1 H, HC=), 5.99 (s, 1 H, Ar), 7.01 (s, 1 H), 9.44 (s, 1 H, CHO), 11.77 (s, 1 H, ArOH) ppm.

Coumarin Dye 18. 4-Pyridylacetic acid hydrochloride (1.79 g, 10.3 mmol) was added with stirring to a solution of compound (3.41 g, 10.3 mmol) in dichloromethane (50 mL). Then NEt$_3$ (2.08 g, 20.6 mmol) was added followed by DCC (2.12 g, 10.3 mmol) and DMAP (126 mg, 1.03 mmol). The reaction mixture was stirred for 48 h, then filtered through a plug of silica gel (with dichloromethane/ether (2/1) as an eluent). After evaporation of solvents, the product 18 ($R_f$=0.07 in dichloromethane) was isolated by column chromatography (with dichloromethane→dichloromethane/ether=3/1 as an eluent). Precipitation from ether gave 2.34 g (52%) of yellow crystals. $^1$H NMR (300 MHz, CDCl$_3$): δ=1.30 (t, J=7.2 Hz, 3 H, CO$_2$CH$_2$CH$_3$), 1.40 (s, 6 H, 2×Me), 1.96 (m, 2 H, NCH$_2$CH$_2$CH$_2$CO$_2$Et), 2.00 (s, 3 H, Me), 2.41 (m, 2 H, NCH$_2$CH$_2$CH$_2$CO$_2$Et), 3.37 (m, 2 H, NCH$_2$CH$_2$CH$_2$CO$_2$Et), 4.20 (q, J=7.2 Hz, 2 H, CO$_2$CH$_2$CH$_3$), 5.32 (s, 1 H, HC=), 6.40 (s, 1 H), 7.08 (s, 1 H), 7.05 (m, 2 H, AA' part of AA'XX' system), 7.82 (s, 1 H, HC=), 8.60 (m, 2 H, XX' part of AA'XX' system) ppm. $\lambda_{abs}$=437 nm, $\lambda_{em}$=507 nm, $\epsilon$=33400 M$^{-1}$cm$^{-1}$, $\Phi_{fl.}$=0.77 (MeOH).

Acid 19. 1 M aq. NaOH (5.4 mL, 5.4 mmol) was added to a warm (+50° C.) solution of ethyl ester 18 (1.54 g, 3.56 mmol) in MeOH/THF mixture (100 mL/100 mL). The reaction mixture was stirred at +50° C. for 1 h; solvents were evaporated in vacuo, the residue was dissolved in water (30 mL), neutralized with 1 M aq. HCl to pH=6, and cooled using an ice-water bath. The precipitate was filtered, washed with cold water and dried affording 0.738 g (51%) of acid 19 as a red solid.

Sulfonic Acid 20-H. 98% $H_2SO_4$ (2 mL) was added to acid 19 (190 mg, 0.47 mmol). The reaction mixture was heated (+35° C.) with stirring for 16 h. After cooling, the reaction mixture was transferred dropwise into the stirred ether/dioxane mixture (100 mL/10 mL). The precipitate was separated by decantation, washed with ether and dried in a flow of nitrogen. The solid material was dissolved in acetone/acetonitrile/water (2.5/2.5/1) mixture, and a red solution was obtained. It was neutralized with a saturated solution of $Na_2HPO_4$, until a green-yellow color appeared. The lower layer (aqueous solution of inorganic salts) was discarded, and the residue was subjected to reversed phase chromatography on Polygogrep 60-50 $C_{18}$ (50 g). The column was eluted with $CH_3CN$/water (4/1) mixture. The fractions containing the first fluorescent spot were evaporated, and the residue was purified additionally by column chromatography on silica gel (acetone/$CH_3CN$/water; 2.5/2.5/1; the sulfonated product 20-H had $R_f$=0.75, while the starting acid 19 $R_f$=0.82). After evaporation of solvents, the residue was precipitated from acetone giving compound 20 (101 mg, 44%, HPLC area 97%). $\lambda_{abs}$=436 nm, $\lambda_{em}$=510 nm, $\epsilon$=25900 $M^{-1}cm^{-1}$, $\Phi_{fl.}$=0.56 (MeOH). $\lambda_{abs}$=436 nm, $\lambda_{em}$=515 nm, $\epsilon$=31200 $M^{-1}cm^{-1}$, $\Phi_{fl.}$=0.57 (in aqueous PBS buffer at pH 7.4).

NHS Ester 20-NHS. Acid 20 (5.0 mg, 10 μmol) was dissolved in DMF (0.5 mL), N-hydroxysuccinimid (1.7 mg, 15 μmol) was added at room temperature followed by HATU (4 mg, 15 μmol) and $NEt_3$ (3.0 mg, 30 μmol). The reaction mixture was stirred at room temperature for 16 h. After that, it was subjected to chromatography without additional work-up (with acetone to acetone/acetonitrile/water (4/4/1) as an eluent). The conjugate with sheep anti-mouse IG had the following properties in PBS buffer at pH 7.4: $\lambda_{abs}$=437 nm, $\lambda_{em}$=512 nm, $\Phi_{fl.}$=0.18, degree of labeling (DOL)=2.7.

Synthesis of Rhodamine Dyes According to Scheme 3:

Rhodamine Dye 22-$CH_2OH$. The fluorinated rhodamine of structure 21 was prepared according to known procedures [a) U.S. Pat. No. 6,372,907; b) K. Kolmakov, V. N. Belay, J. Bierwagen, C. Ringemann, V. Müller, C. Eggeling, S. W. Hell, Chem.—Eur. J. 2010, 16, 158-166]. In a typical experiment, rhodamine 21 (0.30 g, 2.7 mmol) was refluxed overnight in a solution containing 3.50 g (32 mmol) of $SeO_2$ in a mixture of dioxane (20 mL) and water (2 mL). The reaction was monitored by TLC on silica gel plates with $CH_3CN$/$CH_2Cl_2$/$H_2O$ (10:1:1) as the mobile phase. The solution was cooled to room temperature, stirred for 10 min with water (80 mL), $CH_2Cl_2$ (200 mL), silica gel (2 g), and filtered. The organic phase was separated, the aqueous phase extracted twice with $CH_2Cl_2$ (40 mL), the combined organic extracts washed with water (80 mL), dried over $Na_2SO_4$, and evaporated to dryness. The residue was dissolved in abs. ethanol (150 mL), chilled to 0° C. (ice bath), and $NaBH_4$ (1.20 g, 12.4 mmol) was added in few portions upon vigorous stirring, which was continued for 45 min. The solution was poured into a flask containing ice cold water (300 mL) and 500 mL $CH_2Cl_2$, well stirred, aqueous phase separated and extracted with $CH_2Cl_2$ (3×100 mL). The combined extract was evaporated, and the residue separated over 200 g of silica gel with $CH_3CN$/$CH_2Cl_2$/$H_2O$ (10:1:1) as a mobile phase. Pure fractions were filtered from $SiO_2$ through Rotilabo® syringe filters (0.22 μm) and evaporated to furnish 167 mg (53%) of rhodamine 22-$CH_2OH$ as a dark blue crystalline solid (HPLC area 94%; HPLC: A/B 50:50→0:100 in 25 min, $t_R$=10 min).

MS (ESI): m/z (positive mode, %)=675 (100%) $[M+H]^+$; HRMS ($C_{38}H_{34}F_4N_2O_5$), 675.2468 (found M+H) 675.2477 (calc.).

Rhodamine 24-Me. Compound 23-Z (1.00 g, 3.78 mmol) in a mixture of absolute ethanol (20 mL) and 5 M HCl solution in isopropanol (0.83 mL, 4.15 mmol) was introduced into a hydrogen flushed Schlenk flask loaded with 0.20 g of palladium on charcoal (10% Pd, oxidized form, VWR International). Vigorous stirring and a slow purge of $H_2$ was maintained for 3 h at RT, until the reaction was complete (TLC-monitoring on silica plates with MeOH/$CH_2Cl_2$ (1:1) as the mobile phase, phosphomolybdic acid solution in ethanol (5%) as the developing reagent). The solution was filtered through Celite®, which was then thoroughly washed with $CH_2Cl_2$. The solvents were evaporated to furnish 0.45 g (77%) of a colorless hygroscopic powder, which was stored at +5° C. and was used without further treatment. The amidation (preparation of 24-Me) was carried out as follows: to a solution of 20 mg (0.03 mmol) of 22-$CH_2OH$ in a stirred mixture of $CH_3CN$ (7 mL) and $CH_2Cl_2$ (3 mL), cooled to −5° C. (bath with a mixture of ice and brine, 1:1) were subsequently added methyl N-methyl-ω-aminobutyrate hydrochloride 23-H (65 mg, 0.39 mmol) in 3 mL $CH_3CN$, then HATU (91 mg, 0.24 mmol) in 2 mL $CH_3CN$, and, finally, $Et_3N$ (0.2 mL, 1.3 mmol) in 2 mL $CH_3CN$. All reagents were introduced through a septum, while an argon atmosphere was maintained. The solution was stirred overnight in an ice-water bath, and the completion of the reaction was checked by TLC on silica plates with MeOH/$CH_2Cl_2$ (1:8) as the mobile phase. Then the reaction was "quenched" with $CH_2Cl_2$ (30 mL) and ice cold water (50 mL), and the organic phase was separated and consequently washed with 0.5 M aq. HCl (40 mL), water (30 mL), 2% aq. $NaHCO_3$ (45 mL), again with water (3×50 mL), dried over $Na_2SO_4$, and evaporated. The crude product was chromatographed two times over 35 g of silica gel with MeOH/$CH_2Cl_2$ (1:20) as a mobile phase to furnish 19 mg (81%) of rhodamine 24-Me as an amorphous dark blue solid (HPLC: A/B 70:30→0:100 in 25 min; $t_R$=17.3 min, HPLC area 96%). MS (ESI): m/z (positive mode, %)=788 (100%) $[M+H]^+$; HRMS: ($C_{44}H_{46}F_4N_3O_6$) 788.3316 (found M+H) 788.3317 (calc.)

Rhodamine 24-H. Methyl ester 24-Me was saponificated in a weakly alkaline solution as follows: 5.5 mg of 24-Me (7 μmol) was dissolved in a mixture of 0.2% aqueous KOH solution (7.5 mL, 0.27 mmol KOH) and THF (3 mL) at room temperature upon sonication in an ultrasonic bath for few minutes and left for 3 hours. Acetic acid (40 mg, 0.66 mmol) was added, and the solution evaporated to one-third of its initial volume (~3 mL) in vacuo at room temperature. The residue was diluted with equal volume of brine, extracted with $CH_2Cl_2$ (5×15 mL), the extract washed with sat. aqueous solution of $NaHCO_3$ (5 mL), evaporated, and subjected to chromatography over silica gel (10 g) with $CH_3CN$/$H_2O$ (5:1→4:1) as the mobile phase to furnish 4.4 mg (81%) of 24-H as an amorphous dark blue solid (HPLC: A/B 70:30→0: 100 in 25 min; $t_R$=15 min, HPLC area 96%). Fractions were filtered from $SiO_2$ through Rotilabo® syringe filters (0.22 μm). Dye 24-H is slightly soluble in water (giving light blue solutions with red fluorescence), well-soluble in MeOH, $CH_3CN$, and chlorinated solvents. MS (ESI): m/z (positive mode, %)=774(70%) $[M+H]^+$; HRMS: ($C_{43}H_{44}F_4N_3O_6$) 774.3170 (found M+H) 774.3167 (calc.).

Rhodamine 24-NHS (N-hydroxysuccinimidyl ester of 24-H). Rhodamine 24-H (1.0 mg, 1.3 μmol), N-hydroxysuccinimide (4 mg, 35 μmol), $Et_3N$ (3 μL, 20 μmol), and HATU (4 mg, 10 μmol) were combined in dry $CH_3CN$ (2 mL) under an argon atmosphere at 0° C. After stirring at room temperature for 15 min, the reaction was complete, as established by TLC (silica gel plates; $CH_3CN/H_2O$ (5:1); $R_f$-values for 24-NHS and 24-H were found to be 0.1 and 0.6, respectively). The reaction solution was neutralized with trifluoroacetic acid (0.15 mL of 1% (v/v) solution in $CH_3CN$, 20 µmol) and loaded straight onto a column with 3 g of silica gel with $CH_3CN/CH_2Cl_2/H_2O$ (10:1:1) as the mobile phase. Pure fractions were filtered from $SiO_2$ through Rotilabo® syringe filters (0.22 µm), stabilized with trifluoroacetic acid (0.10 mL of 1% solution) and evaporated in vacuo at room temperature to furnish 2 mg of an amorphous solid material containing 24-NHS (HPLC: A/B 70:30→0:100 in 25 min; $t_R$=18 min, detection at 636 nm; HPLC area above 85%) and variable amounts of N-hydroxysuccinimide. MS (ESI): m/z (positive mode, %)=871(100%) $[M+H]^+$; HRMS: $(C_{47}H_{47}F_4N_4O_8)$ 871.3326, (found M+H) 871.3325 (calc.). The active ester was stored under argon at −20° C. and used for immunolabeling experiments without further purification.

Rhodamine 25. Rhodamine 24-Me (21 mg, 0.027 mmol) in abs. THF (7 mL) under an argon atmosphere was treated with following reagents: diallyl N,N-diisopropylphosphoramidite (90 mg, 0.36 mmol), 0.45 M commercial tetrazole solution in acetonitrile (0.80 mL, 0.36 mmol) and, after additional 2 h stirring at room temperature, 5-6 M commercial t-butyl hydroperoxide solution in n-octane (0.15 mL, 0.75 mmol). The progress of the reactions was monitored by TLC on silica plates with $MeOH/CH_2Cl_2$ (1:8) as the mobile phase, and HPLC. The stirring was continued for 1 h, the solution was diluted with $CH_2Cl_2$ (70 mL), the organic phase washed consequently with water (50 mL), 0.05 M aq. HCl (50 mL), 2% aq. $NaHCO_3$ (50 mL), dried and chromatographed over a column with 25 g of silica gel and $CH_2Cl_2/MeOH$ (15:1→5:1) as the mobile phase. Pure fraction were combined, filtered from $SiO_2$ through Rotilabo® syringe filters (0.22 µm) and evaporated to furnish 28 mg (96%) of rhodamine 25 as an amorphous dark blue solid (HPLC: A/B 70:30→0:100 in 25 min; $t_R$=18 min, HPLC area 94%,). MS (ESI): m/z (positive mode, %)=1109 (100%) $[M+H]^+$; HRMS: $(C_{56}H_{64}F_4N_3O_{12}P_2)$ 1108.3897 (found M+H) 1108.3896 (calc.).

Rhodamine 26-Me. Compound 25 (25 mg, 0.022 mmol) in a mixture of abs. THF (25 mL) and $CH_3CN$ (10 mL) was combined with the following reagents: triethyl ammonium formate (0.5 M in THF, 0.50 mL, 0.25 mmol $Et_3N.HCOOH$), formic acid (0.5 M in THF, 0.50 mL, 0.25 mmol HCOOH), triphenylphosphine (0.1 M in THF, 1.0 mL, 100 mmol $Ph_3P$) and tetrakis(triphenylphosphine)palladium(0) (18 mg, 0.016 mmol $Pd(PPh_3)_4$). The solution was stirred overnight at room temperature under an argon atmosphere and at 40° C. for approx. 40 min, until the reaction was complete. The reaction course was monitored by TLC on silica plates with $CH_3CN/H_2O$ (5:1) as a mobile phase and HPLC (see below for details). The reaction mixture was cooled to room temperature, diluted with 8 mL of water containing 1.25 mL 1 M HCl (1.25 mmol HCl). A dark blue precipitate dissolved, and the solution was evaporated to the volume of 5-7 mL in vacuo at room temperature. The residue was diluted with water (5 mL) and $CH_3CN$ (5 mL), acidified with an additional amount (0.6 mL) of 1 M HCl, and loaded onto a column with reverse-phase silica gel (Polygoprep 60-50 $C_{18}$) and water as a mobile phase. The column was eluted consequently with water (50 mL), 0.03 M aq. HCl (100 mL), water containing 0.1% (v/v) $CF_3COOH$ (100 mL), and $CH_3CN→H_2O$ (1:1) containing 0.1% $CF_3COOH$ (150 mL). Pure fractions were combined, filtered from $SiO_2$ through Rotilabo® syringe filters (0.22 µm) and evaporated to furnish 18.5 mg (89%) of rhodamine 6-Me as a dark-blue amorphous material (HPLC: A/B 70:30→0:100 in 25 min; $t_R$=10 min., detection at 636 nm, HPLC area 97%). MS (ESI): m/z (negative mode, %)=946 (100%) $[M-H]^-$; HRMS: $(C_{44}H_{47}F_4N_3O_{12}P_2)$ 946.2648 (found M−H) 946.2644 (calc.).

Rhodamine 26-H. Rhodamine 26-Me (18 mg, 0.019 mmol) was dissolved in a mixture of 0.2% aqueous KOH solution (25 mL, 0.90 mmol KOH) and THF (5 mL) at room temperature upon sonication for a few minutes in an ultrasonic bath and left overnight. Trifluoroacetic acid (0.20 mL, 2.6 mmol) was added, and the solution evaporated to the volume of 10 mL in vacuo at room temperature. The solution (with a precipitate) was diluted with $CH_3CN$ (5 mL) and loaded onto a column containing 12 g of reverse-phase silica gel (Polygoprep 60-50 C18) with water as a mobile phase. The column was first eluted with water (100 mL), then the dye was washed off with $CH_3CN/H_2O$ (1:1) containing 0.1% (v/v) of $CF_3COOH$. Pure fractions were evaporated and subjected to additional purification over a column with regular silica gel (35 g) and $CH_3CN/H_2O$ mixture (5:1→3:1) as a mobile phase. Double filtration (through Rotilabo® syringe filters 0.45 and 0.22 µm) and evaporation of the pure fractions (HPLC-control, detection at 254 nm) furnished 16.5 mg (93%) of compound 26-H (free acid) as a dark blue crystalline solid, well-soluble in aq. $NaHCO_3$, alkali, $Et_3N$, and PBS buffers, MeOH, insoluble in acetone, $CH_3CN$, chloroform (HPLC: A/B 70:30→0:100 in 25 min; $t_R$=8 min, and with A/B 80:20→50:50 in 25 min; $t_R$=20.5 min, detection at 254 nm, HPLC area 99%). $^1H$ NMR (600 MHz, $D_2O$; two amide rotamers in ca. 1:1 ratio): δ=6.80/6.90 (s×2, 2 H, $H^{ar.}$), 6.03/6.05 (s×2, 2 H, C$\underline{H}$=), 4.51 (m, 2 H, $CH_2O$), 3.38/3.58 (m×2, 2 H, $CH_2N$), 3.32 (m, 4 H, 2×$CH_2$ N), 2.85/2.83 (s×2, 3 H, NMe), 2.36 (m, 2 H, $CH_2CO$), 1.80/1.89 (m×2, 4 H, $CH_2$), 1.43/1.46/1.52/1.53 (s×4, 12 H, $CH_3$), 1.16/1.25 (m×2, 2 H, $CH_2C\underline{H}_2CH_2$) ppm; MS (ESI): m/z (negative mode, %)=932 (100%) $[M-H]^-$; HRMS: $(C_{43}H_{45}F_4N_3O_{12}P_2)$ 932.2341 (found M−H) 932.2342 (calc.).

N-hydroxysuccinimidyl ester 26-NHS. In a typical experiment, a portion of rhodamine 26-H, as a stock solution in dry DMF (c=mg/mL, 0.3 mL, 0.32 µmol 26-H; also containing $Et_3N$ as a base, c=4 mg/mL, 12 µmol $Et_3N$) was reacted with TSTU (2 mg, 7 µmol) under an argon atmosphere. After the reaction was complete (30-60 min), as determined by HPLC, the solution was carefully evaporated in vacuo at room temperature and subjected to chromatography over a column with 1 g of silica gel with $CH_3CN/H_2O$ mixture (10:1→3:1) as a mobile phase. N-Hydroxysuccinimide (5 mg, 43 µmol) was dissolved in the combined colored fractions; they were filtered from $SiO_2$ through Rotilabo® syringe filters (0.22 µm), concentrated in vacuo at room temperature, and lyophilized to furnish an amorphous powder that contained N-hydroxysuccinimidyl ester 26-NHS (HPLC: A/B 70:30→0:100 in 25 min; $t_R$=10 min, and with A/B 80:20→50:50 in 25 min; $t_R$=24 min, HPLC area ca. 90%), and variable amounts of N-hydroxysuccinimide. This material was stored at −20° C. and used for immunolabeling without further treatment as a stock solution in DMF (also stored at −20° C.). The pure ester 26-NHS was isolated by preparative HPLC on an 8×250 mm column (A/B 70:30→0:100 in 25 min; 4 mL/min); HPLC area: >90% (254 nm). MS (ESI): m/z (positive mode, %)=1031 (100%) $[M+H]^+$, 1053 (40%) $[M+Na]^+$; HRMS: $(C_{47}H_{48}F_4N_4O_{14}P_2)$ 1031.2645 (found M+H) 1031.2651 (calc.).

EXAMPLE 2

Optical Microscopy Studies of Phosphorylated Fluorescent Dyes of the Invention

FIG. 1 shows confocal and STED microscopy images of vimentin (red) and tubulin (green) filaments in a fixed mammalian PtK2 (*Potorous tridactylus*, kidney) cell. The vimentin skeleton was immunolabeled with NHS ester 12 (dye 11, Table 1); excitation with 405 nm laser. The tubulin skeleton was immunolabeled with Oregon Green™ 488; excitation with 490 nm. The excitation of both dyes was alternated to separate the fluorescence in time. Detection at 510-560 nm for both dyes; STED at 590 nm (STED power 84 mW at backfocal plane); (Scale bars 500 nm)

Figure 2:
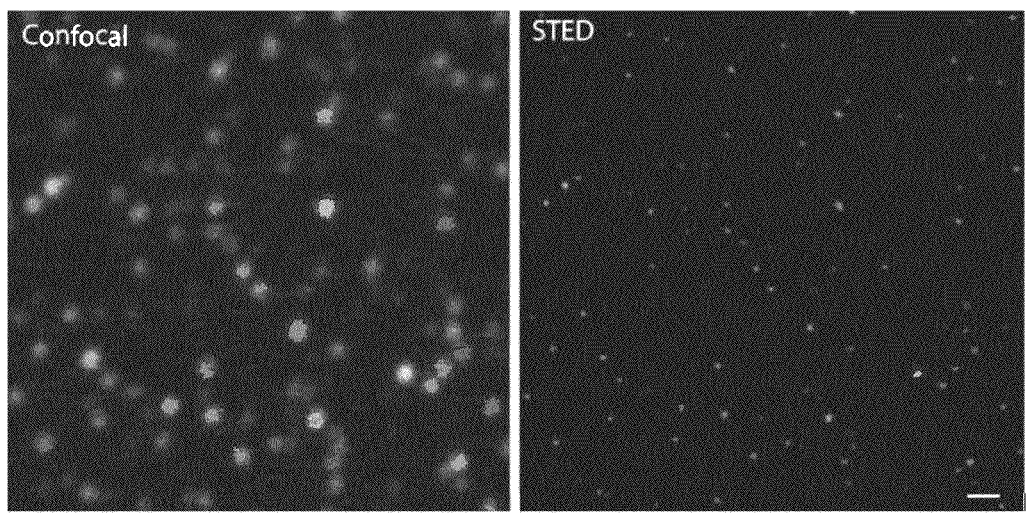
FIG. 2 shows confocal and STED microscopy images of single antibodies in the background to determine the resolution of FIG. 2. Confocal resolution ~200 nm, STED resolution ~50 nm in both channels (red: NHS ester 12, green: Oregon Green™ 488). (Scale bar 500 nm)

FIG. 2 shows confocal and STED microscopy images of single antibodies in the background to determine the resolution of FIG. 2. Confocal resolution ~200 nm, STED resolution ~50 nm in both channels (red: NHS ester 12, green: Oregon Green™ 488). (Scale bar 500 nm)

FIG. 1 illustrates the usefulness of the hydrophilic coumarin dyes with large Stokes shifts in multicolor fluorescence microscopy and STED nanoscopy. Imaging and colocalization of tubuline and vimentin filaments (stained with dye 11 and Oregon Green™ 488, respectively) were achieved using one detection channel and two excitation sources (405 and 488 nm lasers, respectively). Under STED conditions, the dye 11 (with 79 nm Stokes shift) of the invention provides an optical resolution of ca. 50 nm (FIG. 2).

FIG. 3A shows confocal (left) and the STED (right) microscopy images of tubulin filaments in a fixed PtK2 cell. The tubulin skeleton was immunolabeled with compound 26-NHS (Scheme 4; dye 26-H in Table 1); excitation with 635 nm diode laser, 17 µW. Detection at 670/40 nm; pulsed STED at 750 nm (STED power ~350 mW); optical resolution: ~300 nm (inset, left) vs. 30 nm (inset, right). 3B. Closeup of the marked region of 3A. The blurred tubulin filaments in the confocal image (left) can be distinguished by STED microscopy (right). This is further emphasized by the intensity profiles along the lines in the images.

Figure 4:
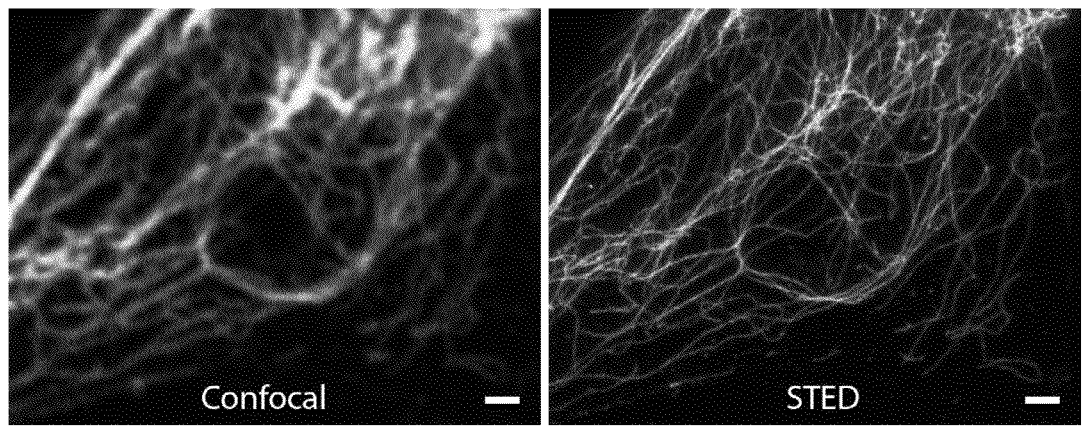
FIG. 4 shows confocal and STED microscopy images of vimentin filaments in a fixed PtK2 cell immunolabeled with 26-NHS (Scheme 4; dye 26-H in Table 1).

FIG. 4 shows confocal and STED microscopy images of vimentin filaments in a fixed PtK2 cell immunolabeled with 26-NHS (Scheme 4; dye 26-H in Table 1); excitation with 647±5 nm from a SC laser, 2 µW. Detection at 670±15 nm; pulsed STED at 745±2 nm (STED power ~30 mW at the backfocal plane); 20 nm pixel; optical resolution: 250 nm (confocal) vs. 50 nm (STED). (Scale bar 1 µm).

Figure 5:
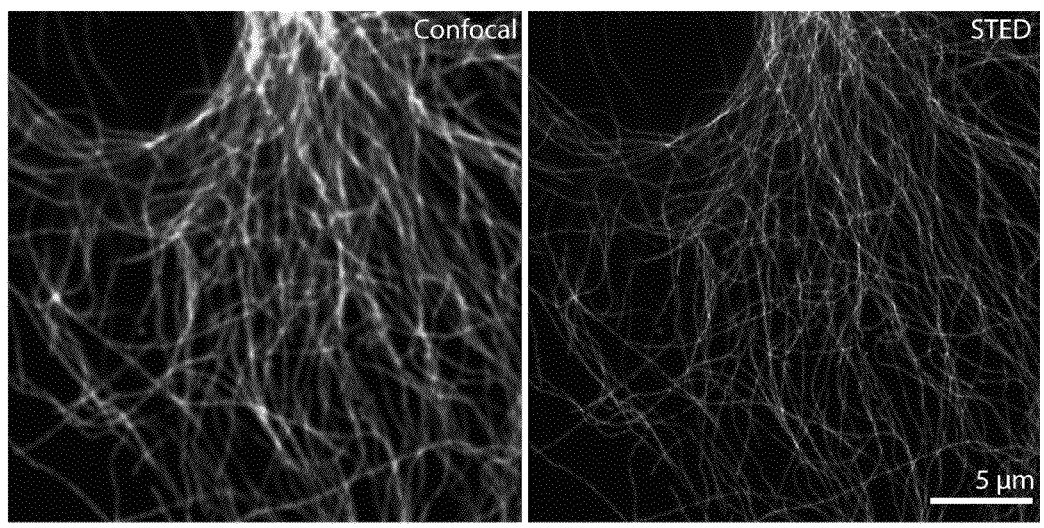
FIG. 5 shows confocal (left) and the STED (right) microscopy images of tubulin filaments in a fixed PtK2 cell. The tubulin skeleton was immunolabeled with compound 24-NHS (Scheme 4; dye 24-H in Table 1).

FIG. 5 shows confocal (left) and the STED (right) microscopy images of tubulin filaments in a fixed PtK2 cell. The tubulin skeleton was immunolabeled with compound 24-NHS (Scheme 4; dye 24-H in Table 1); excitation with 635 nm diode laser, 17 µW. Detection at 670/40 nm; pulsed STED at 750 nm (STED power ~350 mW).

Figure 3:
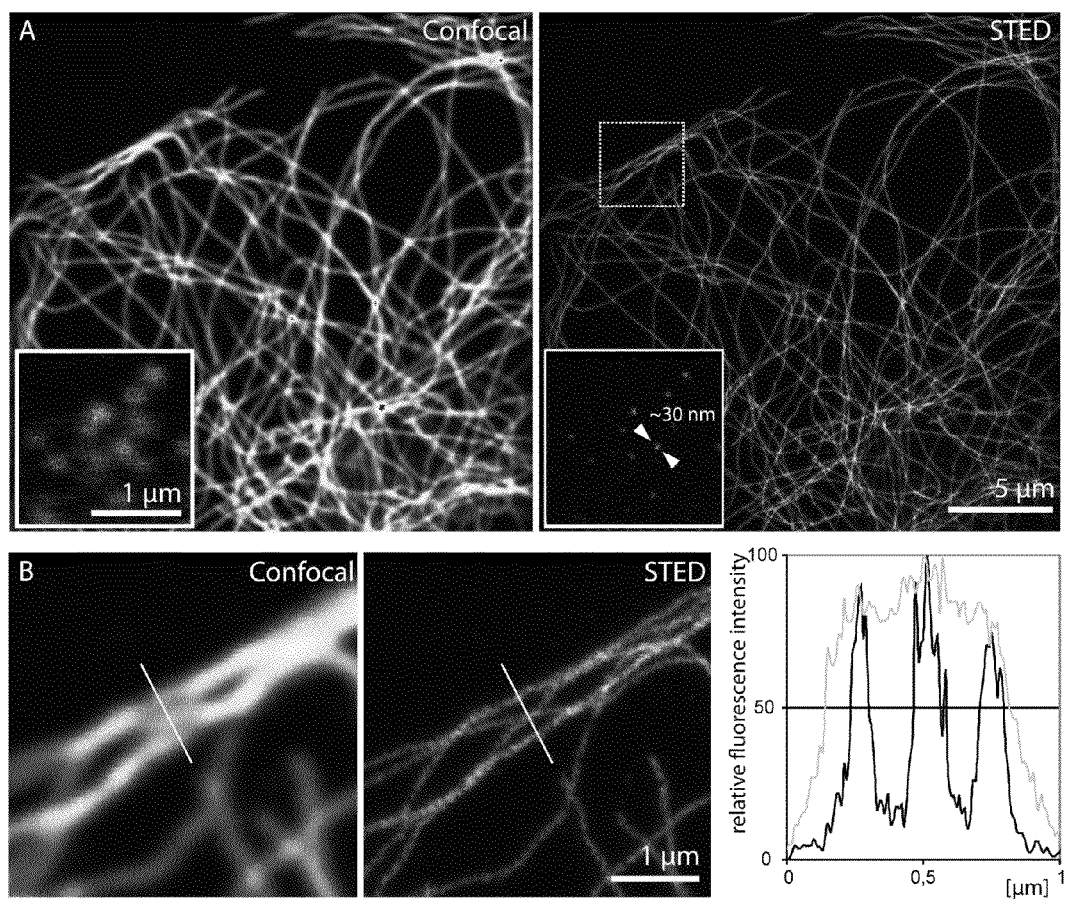
FIG. 3A shows confocal (left) and the STED (right) microscopy images of tubulin filaments in a fixed PtK2 cell. The tubulin skeleton was immunolabeled with compound 26-NHS (Scheme 4; dye 26-H in Table 1)
FIG. 3B shows a closeup of the marked region of 3A.

The rhodamine dye 26-H decorated with two primary phosphate groups emits red light in the near IR region where the autofluorescence of cells and their organelles is negligible (FIGS. 3 and 4). The core fluorophore of this dye is very lipophilic (e.g. compound 21). Many lipophilic (nonpolar) fluorescent dyes are known to aggregate or participate in the unspecific labeling of various cell organelles (e.g. mitochondria, endoplasmatic reticulum, etc.). These undesired events may result in a considerable fluorescence background of an image. The presence of the hydrophilic phosphoric acid groups in dyes 11 and 26 effectively prevents their aggregation in aqueous solutions and eliminates the unspecific labeling (no background fluorescence was detected in FIG. 3 and only very little background fluorescence is seen in FIG. 4). Even the presence of two non-phosphorylated hydroxy groups in compound 24-H prevents aggregation of this dye in aqueous buffers, blocks its non-specific binding with proteins and provides microscopic images (confocal and STED) without considerable background (FIG. 5). However, the relative brightness of the images in FIG. 5 is lower than the brightness of the images in FIGS. 3 and 4 (obtained with phosphorylated compound 26-H/26-NHS). [The color table is not shown.]

Under STED conditions, the dyes of the invention (e.g. compounds 11, 24, and 26) provide an optical resolution below the diffraction limit (50-75 nm depending on the actual implementation of the STED microscope and the power of the STED laser).

Summarizing, the present invention introduces new fluorescent dyes substituted with one or more phosphorylated hydroxy groups [CH$_2$OP(O)(OH)$_2$] or phosphonic acid moieties. Methyl groups attached to the position C-4 of the 2,2,4-trimethyl-1,2-dihydroquinoline fragments incorporated into coumarins and rhodamines were oxidized with SeO$_2$, and then reduced with NaBH$_4$ (to yield CH$_2$OH-groups). Then the hydroxymethyl groups were phosphorylated. This phosphorylation procedure is also applicable to BODIPY dyes with CH$_2$OH groups. In solutions, O-phosphorylated or C-hydroxylated coumarins and rhodamines were found to have high fluorescence quantum yields in the free state and after conjugation with proteins (in aqueous buffers). In "superresolution" light microscopy (e.g. under conditions of stimulated emission depletion), the disclosed fluorescent dyes provide the optical resolution of 30-75 nm with a low background signal. Additionally, due to their large Stokes shifts and high photostabilities, the phosphorylated coumarins allow to combine the multilabel imaging (using one detector and several excitation sources) with the diffraction unlimited optical resolution.

The invention claimed is:
1. A fluorescent dye comprising a phosphorylated hydroxymethyl group selected from the group consisting of compounds of the following general formulae Ia-Ib:

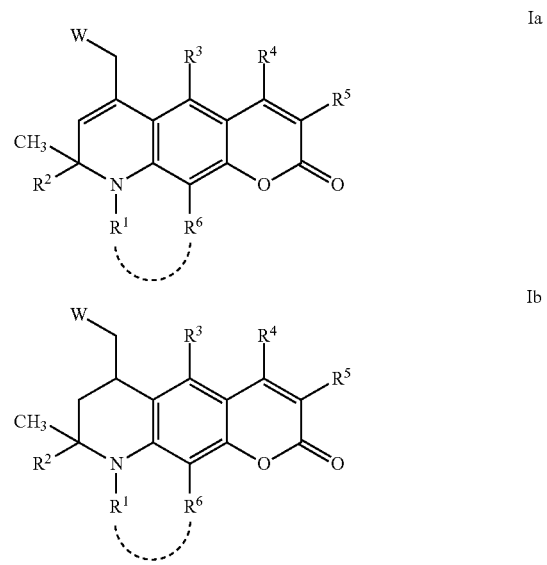

wherein
R$^1$ denotes H, CH$_3$, C$_2$H$_5$, any other alkyl, cycloalkyl, alkenyl, alkynyl, aryl, arylalkyl or heteroaryl group; (functionally) substituted alkyl, cycloalkyl, alkenyl, alkynyl, aryl, arylalkyl or heteroaryl group; heterosubstituted alkyl or cycloalkyl group; or R$^1$ may represent a combination of the said groups;
R$^2$=CH$_3$, alkyl, HOCH$_2$, hydroxyalkyl, or alkoxyalkyl;
R$^3$ and R$^6$ independently denote H, F, Cl, CH$_3$, or any other alkyl group; alternatively, R$^1$ - - - R$^6$=—(CH$_2$)$_2$—, —(CH$_2$)$_3$—, —CH$_2$COCH$_2$—, —CH$_2$[C=N(OR$^a$)]CH$_2$— or —CH$_2$(C=N—NR$^a$R$^b$)CH$_2$—, with R$^a$ and R$^b$ independently denoting separate substituents of R$^a$ and R$^b$ forming a cyclic system only in the case of secondary amides, where R$^1$=(CH$_2$)$_m$CONR$^a$R$^b$, or (CH$_2$CH$_2$O)$_m$CONR$^a$R$^b$, or R$^1$=(CH$_2$)$_m$CH$_2$OP(O)(NR$^a$R$^b$)(NR$^c$R$^d$);

R$^4$=H, CH$_3$, alkyl, OR$^a$, (CH$_2$)$_m$COOR$^a$, (CH$_2$)$_m$CH$_2$OR$^a$, (CH$_2$)$_m$COOR$^a$, or (CH$_2$)$_m$CONR$^a$R$^b$ (m=0-23), with R$^a$— and R$^b$ as defined above;

R$^5$=aryl, heteroaryl; (functionally) substituted aryl or heteroaryl, CF$_3$, perfluoro-alkyl (C$_n$F$_{2n+1}$), CN, C≡CR$^a$, with the definition of R$^a$ as given above;

W=OP(O)Y$^1$Y$^2$ or P(O)Y$^1$Y$^2$, where Y$^1$ and Y$^2$ independently denote any of the following residues: OH, O(-), OR$^a$ and OR$^b$, NHR$^a$ and NHR$^b$, NR$^a$R$^b$ and NR$^c$R$^d$, OR$^a$ and NHR$^b$, OR$^a$ and NR$^b$R$^c$, NHR$^a$ and NR$^b$R$^c$;

and any salt thereof.

2. The fluorescent dye of claim 1, having one of the following formulae:

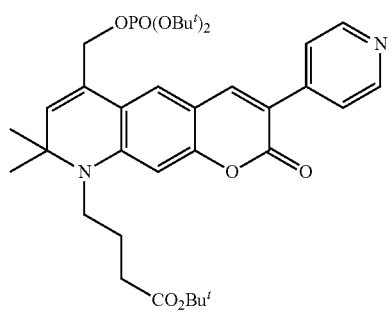

10

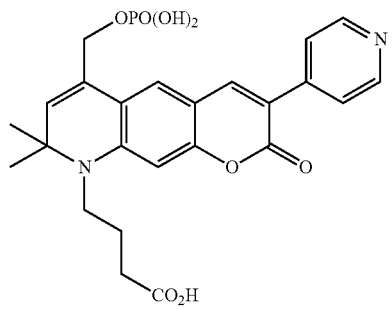

11

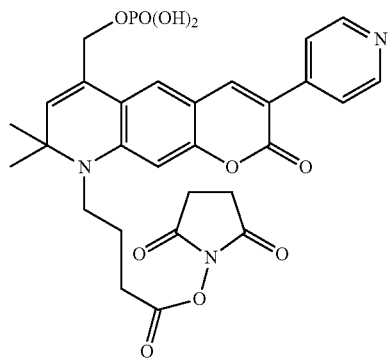

12

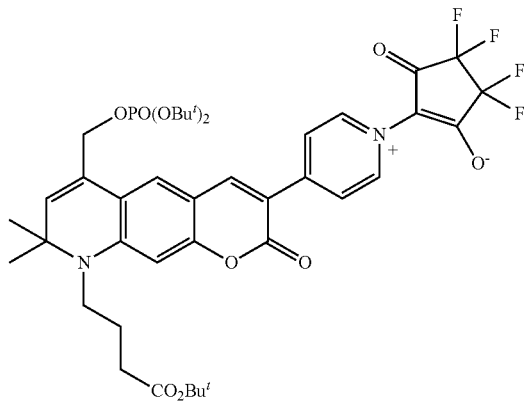

13

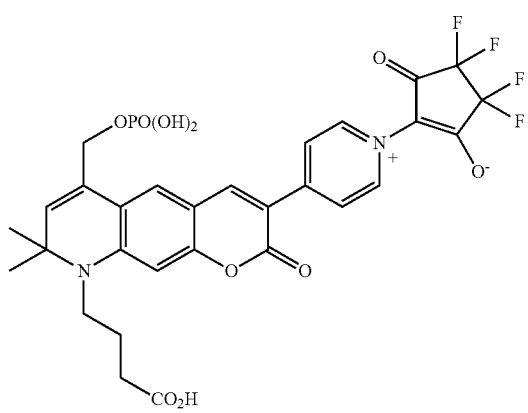

14

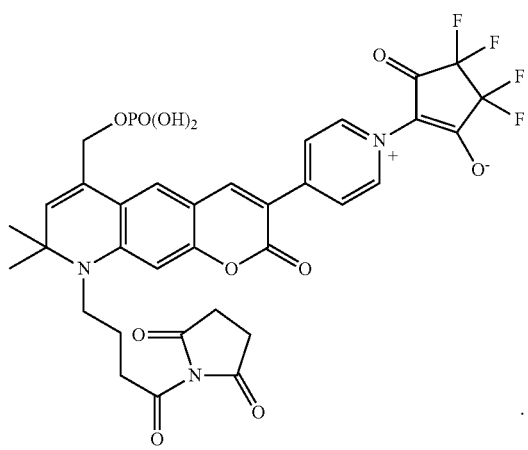

15

3. A method for preparing a fluorescent dye according to claim 1, comprising the following steps:
 a) providing a precursor compound wherein W in formulae Ia-Ib is replaced by a reactive group W' selected from the group consisting of halogen (Cl, Br, I), hydroxy (OH), ether (OR$^a$), acyloxy (OCOR$^a$), or sulfonyloxy (OSO$_2$R$^a$) residues; with R$^a$ defined as in claim 1 above;
 b) reacting said group W' of the precursor compound with a phosphorylating agent to obtain the fluorescent dye; and
 c) optionally performing post-synthetic modifications of the (protected) phosphate group.

4. The method of claim 3, wherein step c) comprises deprotection of a tertiary phosphate ester with two equal groups to obtain a target compound with a primary phosphate group or, alternatively, saponification of the tertiary phosphate group to obtain a secondary phosphate group; and, optionally, amidation of the primary or secondary phosphate group in a presence of an amine and a coupling reagent to obtain a functionally substituted amide (or amido ester) of the target phosphoric acid.

5. A precursor compound for preparing a fluorescent dye of the following general formulae Ia-Ib

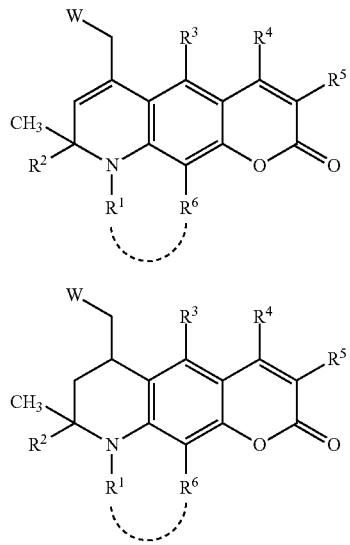

wherein
- $R^1$ denotes H, $CH_3$, $C_2H_5$, any other alkyl, cycloalkyl, alkenyl, alkynyl, aryl, arylalkyl or heteroaryl group; (functionally) substituted alkyl, cycloalkyl, alkenyl, alkynyl, aryl, arylalkyl, or heteroaryl group; heterosubstituted alkyl or cycloalkyl group; or $R^1$ may represent a combination of the said groups;
- $R^2$=$CH_3$, alkyl, $HOCH_2$, hydroxyalkyl, or alkoxyalkyl;
- $R^3$ and $R^6$ independently denote H, F, Cl, $CH_3$, or any other alkyl group; alternatively, $R^1$ - - - $R^6$=—$(CH_2)_2$—, —$(CH_2)_3$—, —$CH_2COCH_2$—, —$CH_2[C=N(OR^a)]CH_2$— or —$CH_2(C=N-NR^aR^b)CH_2$—, with $R^a$ and $R^b$ independently denoting separate substituents or $R^a$ and $R^b$ forming a cyclic system only in the case of secondary amides, where $R^1$=$(CH_2)_mCONR^aR^b$, or $(CH_2CH_2O)_mCONR^aR^b$, or $R^1$=$(CH_2)_mCH_2OP(O)(NR^aR^b)(NR^cR^d)$;
- $R^4$=H, $CH_3$, alkyl, $OR^a$, $(CH_2)_mCOOR^a$, $(CH_2)_mCH_2OR^a$, $(CH_2)_mCOOR^a$, or $(CH_2)_mCONR^aR^b$ (m=0-23), with $R^a$ and $R^b$ as defined above;
- $R^5$=aryl, heteroaryl; (functionally) substituted aryl or heteroaryl, $CF_3$, perfluoro-alkyl ($C_nF_{2n+1}$), CN, C≡$CR^a$, with the definition of $R^a$ as given above;
- W=halogen (Cl, Br, I), hydroxy (OH), ether ($OR^a$, preferably aryl ether), acyloxy ($OCOR^a$), or sulfonyloxy ($OSO_2R^a$) residues.

6. A precursor compound according to claim 5 having one of the following formulae:

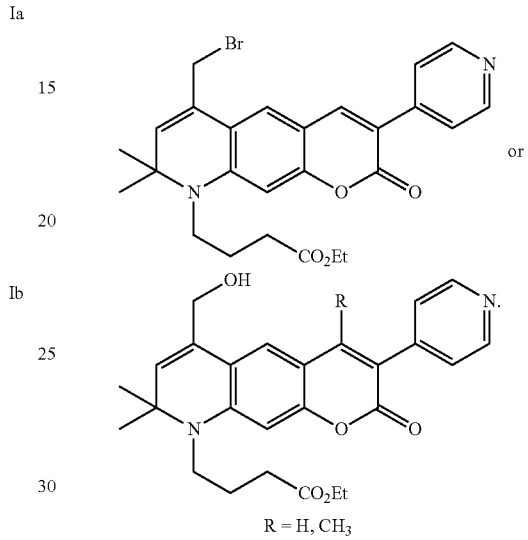

R = H, $CH_3$

7. A method of using a fluorescent dye according to claim 1, or a stable conjugate thereof with an organic substance.

8. The method according to claim 7, wherein the fluorescent dye is used in spectroscopy, far-field optical microscopy fluorescence correlation spectroscopy, ground state depletion with individual molecular return (GSDIM) imaging methods, fluorescence lifetime imaging (FLIM), as a donor or an acceptor in fluorescent resonance energy transfer studies, or confocal microscopy.

9. The method according to claim 7, wherein the fluorescent dye is in free form or attached to organic substances or biomolecules, and is used in multimodal or multicolor imaging and co-localization techniques based on Stokes shifts observed in an optical microscope.

10. The method according to claim 9 wherein a first said fluorescent dye has a Stokes shift of 10-30 nm and a second said fluorescent dye has a Stokes shift of 50-200 nm.

* * * * *